United States Patent
Park et al.

(10) Patent No.: US 12,188,026 B2
(45) Date of Patent: Jan. 7, 2025

(54) **SURFACE EXPRESSION VECTOR USING POLY-GAMMA-GLUTAMATE SYNTHETIC GENE DERIVED FROM STRAIN IN *BACILLUS*, AND METHOD FOR EXPRESSING PROTEIN ON SURFACE OF MICROORGANISM, USING SAME**

(71) Applicant: BIOLEADERS CORPORATION, Yongin-si (KR)

(72) Inventors: Young Chul Park, Seoul (KR); Jae Won Jeon, Seoul (KR); Hong Gyu Park, Seoul (KR); Hyun Jun Kang, Goyang-si (KR); Se Eun Byeon, Hwaseong-si (KR); Kwang Seo Park, Goyang-si (KR); Dae Eun Ki, Seoul (KR)

(73) Assignee: BIOLEADERS CORPORATION, Yongin-si (KR)

( * ) Notice: Subject to any disclaimer, the term of this patent is extended or adjusted under 35 U.S.C. 154(b) by 785 days.

(21) Appl. No.: 17/253,259

(22) PCT Filed: Jun. 24, 2019

(86) PCT No.: PCT/KR2019/007592
§ 371 (c)(1),
(2) Date: Dec. 17, 2020

(87) PCT Pub. No.: WO2020/004877
PCT Pub. Date: Jan. 2, 2020

(65) Prior Publication Data
US 2022/0090099 A1    Mar. 24, 2022

(30) Foreign Application Priority Data
Jun. 26, 2018 (KR) .................. 10-2018-0073345

(51) Int. Cl.
*C12N 15/74* (2006.01)
*C12N 9/12* (2006.01)

(52) U.S. Cl.
CPC ......... *C12N 15/746* (2013.01); *C12N 9/1288* (2013.01); *C12Y 207/08005* (2013.01)

(58) Field of Classification Search
CPC ............ C12N 15/746; C12N 9/1288; C12Y 207/08005
See application file for complete search history.

(56) References Cited

U.S. PATENT DOCUMENTS 7,553,636 B2 * 6/2009 Sung .............. C12Y 207/08005 435/69.7

FOREIGN PATENT DOCUMENTS

| EP | 2386645 | 11/2011 |
|---|---|---|
| KR | 20040032824 | 4/2004 |
| KR | 20040034780 | 4/2004 |
| KR | 20080086161 | 9/2008 |
| WO | 2003014360 | 2/2003 |
| WO | 2006126682 | 11/2006 |

OTHER PUBLICATIONS

Kodama et al. 2007 "Bacillus subtilis AprX Involved in Degradation of a Heterologous Protein During the Late Stationary Growth Phase", Journal of Bioscience and Bioengineering. vol. 104(2):135-143 (Year: 2007).*
Sawada "Poly-L-gamma-glutamic acid production by recombinant Bacillus subtilis without pgsA gene" AMB Expr (2018) 8(110): 1-11 (Year: 2018).*
Lee et al. 2010."Human papillomavirus type 16 E6-specific antitumor immunity is induced by oral administration of HPV16 E6-expressing Lactobacillus casei in C57BL/6 mice", Cancer Immunol Immunother, vol. 59: 1727-1737. (Year: 2010).*
Urushibata "Characterization of the Bacillus subtilis ywsC Gene, Involved in Y-Polyglutamic Acid Production" Journal of Bacteriology (2002) 184 (2): 337-343. (Year: 2002).*
Agterberg, et al., Outer membrane PhoE protein of *Escherichia coli* as a carrier for foreign antigenic determinants: immunogenicity of epitopes of foot-and-mouth disease virus, Vaccine, Feb. 1990, vol. 8, pp. 85-91.
Ashiuchi, et al., A Poly-γ-glutamate Synthetic System of Bacillus subtilis IFO 3336: Gene Cloning and Biochemical Analysis of Poly-γ-glutamate Produced by *Escherichia coli* Clone Cells, Biochemical and Biophysical Research Communications, 1999, vol. 263, No. 1, pp. 6-12.
Bacillus subtilis strain B-115 PsgA (pgsA) gene, complete cds.
Bacillus subtilis strain GXA-28 poly-gamma-glutamate synthase subunit PgsB (pgsB), polygamma-glutamate synthase subunit PgsC (pgsC), poly-gamma-glutamate synthase subunit PgsA (pgsA), and poly-gamma-glutamate synthase subunit PgsE (pgsE) genes, complete cds.
Charbit, et al., Presentation of two epitopes of the preS2 region of hepatitis B virus on live recombinant bacteria, The Journal of Immunology, Sep. 1, 1987, vol. 139, No. 5, pp. 1658-1664.
Felici, Selection of Antibody Ligands from a Large Library of Oligopeptides Expressed on a Multivalent Exposition Vector, J. Mol. Biol., 1991, vol. 222, pp. 301-310.
Francisco, et al., Transport and anchoring of β-lactamase to the external surface of *Escherichia coli*, Proc. Natl. Acad. Sci., Apr. 1992, vol. 89, pp. 2713-2717.
Fuchs, et al., Targeting Recombinant Antibodies to the Surface of *Escherichia coli*: Fusion to a Peptidoglycan Associated Lipoprotein, Bio/Technology, Dec. 1991, vol. 9, pp. 1369-1372.

(Continued)

*Primary Examiner* — Neil P Hammell
*Assistant Examiner* — Kelly Nichet Hassell
(74) *Attorney, Agent, or Firm* — CANTOR COLBURN LLP

(57) ABSTRACT

Provided is a surface expression vector having pgsA, a gene encoding poly-gamma-glutamate synthetase, and a method of expressing a target protein on the microbial surface using the vector. The vector having foreign genes inserted therein is transformed into a microorganism and allows a foreign protein to be stably expressed on the surface of the microorganism.

14 Claims, 10 Drawing Sheets

Specification includes a Sequence Listing.

(56) References Cited

OTHER PUBLICATIONS

Georgiou, et al., Practical applications of engineering Gram-negative bacterial cell surfaces, TIBTECH, Jan. 1993, vol. 11. pp. 6-10.
Hedegaard, et al., Type 1 fimbriae of *Escherichia coli* as carriers of heterologous antigenic sequences, Gene, 1989, vol. 85, pp. 115-124.
Jung, et al., Expression of carboxymethylcellulase on the surface of *Escherichia coli* using Pseudomonas syringae ice nucleation protein, Enzyme and Microbial Technology, Apr. 1998, vol. 22, pp. 348-354.
Jung, et al., Surface Display of Zymomonas mobilis levansucrase by using the ice-nucleation protein of Pseudomonas syringae, Nature Biotechnology, Jun. 1998, vol. 16, pp. 576-580.
Klauser, et al., Extracellular transport of cholera toxin B subunit using Neisseria IgA protease β-domain: conformation dependent outer membrane translocation, The EMBO Journal, 1990, vol. 9, No. 6, pp. 1991-1999.
Ko, et al., Effects of Glucose and Glycerol on γ-Poly(glutamic acid) Formation by Bacillus licheniformis ATCC 9945a, Biotechnology and Bioengineering, Feb. 20, 1998, vol. 57, No. 4, pp. 430-437.
Kornacker, et al., The normally periplasmic enzyme β-lactamase is specifically and efficiently translocated through the *Escherichia coli* outer membrane when it is fused to the cell-surface enzyme pullulanase, Molecular Microbiology, 1990, vol. 4, No. 7, pp. 1101-1109.
Lee, et al., Microbial cell-surface display, Trends in Biotechnology, Jan. 2003, vol. 21, No. 1, pp. 45-52.
Lee, et al., Surface-displayed viral antigens on *Salmonella* carrier vaccine, Nature Biotechnology, Jun. 2000, vol. 18, pp. 645-648.
Makino, et al., Molecular Characterization and Protein Analysis of the cap Region, Which Is Essential for Encapsulation in Bacillus anthracis, Journal of Bacteriology, Feb. 1989, vol. 171, No. 2, pp. 722-730.
Narita, et al., Display of active enzymes on the cell surface of *Escherichia coli* using PgsA anchor protein and their application to bioconversion, Appl Microbiol Biotechnol, 2006, vol. 70, pp. 564-572.
Newton, et al., Immune Response to Cholera Toxin Epitope Inserted in *Salmonella* Flagellin, Science, Apr. 1989, vol. 244, pp. 70-72.
Samuelson, et al., Cell Surface Display of Recombinant Proteins on *Staphylococcus carnosus*, Journal of Bacteriology, Mar. 1995, vol. 177, No. 6, pp. 1470-1476.
International Search Report—PCT/KR2019/007592 dated Oct. 18, 2019.

\* cited by examiner

SEQUENCE LISTING

<160> NUMBER OF SEQ ID NOS: 26

<210> SEQ ID NO 1
<211> LENGTH: 31
<212> TYPE: DNA
<213> ORGANISM: Artificial sequence
<220> FEATURE:
<223> OTHER INFORMATION: PCR primer

<400> SEQUENCE: 1
tggtggatcc gtgagcaagg gcgaggagct g                                    31

<210> SEQ ID NO 2
<211> LENGTH: 47
<212> TYPE: DNA
<213> ORGANISM: Artificial sequence
<220> FEATURE:
<223> OTHER INFORMATION: PCR primer

<400> SEQUENCE: 2
tgactctaga actagtgtcg acggtacctt acttgtacag ctcgtcc                   47

<210> SEQ ID NO 3
<211> LENGTH: 34
<212> TYPE: DNA
<213> ORGANISM: Artificial sequence
<220> FEATURE:
<223> OTHER INFORMATION: PCT primer

<400> SEQUENCE: 3
tcgagcatgc aatacccact tattgcgatt tgct                                 34

<210> SEQ ID NO 4
<211> LENGTH: 74
<212> TYPE: DNA
<213> ORGANISM: Artificial sequence
<220> FEATURE:
<223> OTHER INFORMATION: PCR primer

<400> SEQUENCE: 4
tacgggatcc accagaacca ccagaaccac cagaaccacc agaaccacct gagagtacgt     60
cgtcagaata cgtt                                                       74

<210> SEQ ID NO 5
<211> LENGTH: 34
<212> TYPE: DNA
<213> ORGANISM: Artificial sequence
<220> FEATURE:
<223> OTHER INFORMATION: PCR Primer

<400> SEQUENCE: 5
tcgagcatgc aatacccact tattgcgatt tgct                                 34

<210> SEQ ID NO 6
<211> LENGTH: 74
<212> TYPE: DNA
<213> ORGANISM: Artificial sequence
<220> FEATURE:
<223> OTHER INFORMATION: PCR primer

<400> SEQUENCE: 6
tacgggatcc accagaacca ccagaaccac cagaaccacc agaaccacct cccatcataa     60
tatcgcctac aaat                                                       74

```
<210> SEQ ID NO 7
<211> LENGTH: 34
<212> TYPE: DNA
<213> ORGANISM: Artificial sequence
<220> FEATURE:
<223> OTHER INFORMATION: PCR primer

<400> SEQUENCE: 7
tcgagcatgc aatacccact tattgcgatt tgct                              34

<210> SEQ ID NO 8
<211> LENGTH: 74
<212> TYPE: DNA
<213> ORGANISM: Artificial sequence
<220> FEATURE:
<223> OTHER INFORMATION: PCR primer

<400> SEQUENCE: 8
tacgggatcc accagaacca ccagaaccac cagaaccacc agaaccacct ttttgctccg   60
ttactttttc aaca                                                    74

<210> SEQ ID NO 9
<211> LENGTH: 34
<212> TYPE: DNA
<213> ORGANISM: Artificial sequence
<220> FEATURE:
<223> OTHER INFORMATION: PCR primer

<400> SEQUENCE: 9
tcgagcatgc aatacccact tattgcgatt tgct                              34

<210> SEQ ID NO 10
<211> LENGTH: 74
<212> TYPE: DNA
<213> ORGANISM: Artificial sequence
<220> FEATURE:
<223> OTHER INFORMATION: PCR primer

<400> SEQUENCE: 10
tacgggatcc accagaacca ccagaaccac cagaaccacc agaaccacct gctacataat   60
ccgaggctct aaag                                                    74

<210> SEQ ID NO 11
<211> LENGTH: 34
<212> TYPE: DNA
<213> ORGANISM: Artificial sequence
<220> FEATURE:
<223> OTHER INFORMATION: PCR Primer

<400> SEQUENCE: 11
tcgagcatgc aatacccact tattgcgatt tgct                              34

<210> SEQ ID NO 12
<211> LENGTH: 74
<212> TYPE: DNA
<213> ORGANISM: Artificial sequence
<220> FEATURE:
<223> OTHER INFORMATION: PCR primer

<400> SEQUENCE: 12
tacgggatcc accagaacca ccagaaccac cagaaccacc agaaccaccg actttctggt   60
acgaaatttt cttt                                                    74

<210> SEQ ID NO 13
```

<211> LENGTH: 180
<212> TYPE: DNA
<213> ORGANISM: Artificial sequence
<220> FEATURE:
<223> OTHER INFORMATION: PgsA1

<400> SEQUENCE: 13

```
atgaaaaaag aactgagctt tcatgaaaag ctgctaaagc tgacaaaaca gcaaaaaaag      60
aaaaccaata agcacgtatt tattgccatt ccgatcgttt ttgtccttat gttcgctttc     120
atgtgggcgg gaaaagcgga aacgccgaag gtcaaaacgt attctgacga cgtactctca     180
```

<210> SEQ ID NO 14
<211> LENGTH: 210
<212> TYPE: DNA
<213> ORGANISM: Artificial sequence
<220> FEATURE:
<223> OTHER INFORMATION: PgsA2

<400> SEQUENCE: 14

```
atgaaaaaag aactgagctt tcatgaaaag ctgctaaagc tgacaaaaca gcaaaaaaag      60
aaaaccaata agcacgtatt tattgccatt ccgatcgttt ttgtccttat gttcgctttc     120
atgtgggcgg gaaaagcgga aacgccgaag gtcaaaacgt attctgacga cgtactctca     180
gcctcatttg taggcgatat tatgatggga                                      210
```

<210> SEQ ID NO 15
<211> LENGTH: 240
<212> TYPE: DNA
<213> ORGANISM: Artificial sequence
<220> FEATURE:
<223> OTHER INFORMATION: PgsA3

<400> SEQUENCE: 15

```
atgaaaaaag aactgagctt tcatgaaaag ctgctaaagc tgacaaaaca gcaaaaaaag      60
aaaaccaata agcacgtatt tattgccatt ccgatcgttt ttgtccttat gttcgctttc     120
atgtgggcgg gaaaagcgga aacgccgaag gtcaaaacgt attctgacga cgtactctca     180
gcctcatttg taggcgatat tatgatggga cgctatgttg aaaaagtaac ggagcaaaaa     240
```

<210> SEQ ID NO 16
<211> LENGTH: 300
<212> TYPE: DNA
<213> ORGANISM: Artificial sequence
<220> FEATURE:
<223> OTHER INFORMATION: PgsA4

<400> SEQUENCE: 16

```
atgaaaaaag aactgagctt tcatgaaaag ctgctaaagc tgacaaaaca gcaaaaaaag      60
aaaaccaata agcacgtatt tattgccatt ccgatcgttt ttgtccttat gttcgctttc     120
atgtgggcgg gaaaagcgga aacgccgaag gtcaaaacgt attctgacga cgtactctca     180
gcctcatttg taggcgatat tatgatggga cgctatgttg aaaaagtaac ggagcaaaaa     240
ggggcagaca gtattttttca atatgttgaa ccgatcttta gagcctcgga ttatgtagca    300
```

<210> SEQ ID NO 17
<211> LENGTH: 564
<212> TYPE: DNA
<213> ORGANISM: Artificial sequence
<220> FEATURE:
<223> OTHER INFORMATION: PgsA5

<400> SEQUENCE: 17

```
atgaaaaaag aactgagctt tcatgaaaag ctgctaaagc tgacaaaaca gcaaaaaaag      60
aaaaccaata agcacgtatt tattgccatt ccgatcgttt ttgtccttat gttcgctttc     120
atgtgggcgg gaaaagcgga aacgccgaag gtcaaaacgt attctgacga cgtactctca     180
gcctcatttg taggcgatat tatgatggga cgctatgttg aaaaagtaac ggagcaaaaa     240
ggggcagaca gtattttca  atatgttgaa ccgatcttta gagcctcgga ttatgtagca     300
ggaaactttg aaaacccggt aacctatcaa agaattata  aacaagcaga taagagatt      360 catctgcaga cgaataagga atcagtgaaa gtcttgaagg atatgaattt cacggttctc     420
aacagcgcca acaaccacgc aatggattac ggcgttcagg gcatgaaaga tacgcttgga     480
gaatttgcga agcaaaacct tgatatcgtt ggagcgggat acagcttaag tgatgcgaaa     540
aagaaaattt cgtaccagaa agtc                                            564
```

<210> SEQ ID NO 18
<211> LENGTH: 38
<212> TYPE: DNA
<213> ORGANISM: Artificial sequence
<220> FEATURE:
<223> OTHER INFORMATION: PCR primer

<400> SEQUENCE: 18

```
cgctggatat ctacatgcac gtatttattg ccattccg                              38
```

<210> SEQ ID NO 19
<211> LENGTH: 74
<212> TYPE: DNA
<213> ORGANISM: Artificial sequence
<220> FEATURE:
<223> OTHER INFORMATION: PCR primer

<400> SEQUENCE: 19

```
tacgggatcc accagaacca ccagaaccac cagaaccacc agaaccacct gagagtacgt      60
cgtcagaata cgtt                                                       74
```

<210> SEQ ID NO 20
<211> LENGTH: 38
<212> TYPE: DNA
<213> ORGANISM: Artificial sequence
<220> FEATURE:
<223> OTHER INFORMATION: PCR primer

<400> SEQUENCE: 20

```
cgctggatat ctacatgcac gtatttattg ccattccg                              38
```

<210> SEQ ID NO 21
<211> LENGTH: 74
<212> TYPE: DNA
<213> ORGANISM: Artificial sequence
<220> FEATURE:
<223> OTHER INFORMATION: PCR primer

<400> SEQUENCE: 21

```
tacgggatcc accagaacca ccagaaccac cagaaccacc agaaccacct cccatcataa      60
tatcgcctac aaat                                                       74
```

<210> SEQ ID NO 22
<211> LENGTH: 38
<212> TYPE: DNA

```
<213> ORGANISM: Artificial sequence
<220> FEATURE:
<223> OTHER INFORMATION: PCR primer

<400> SEQUENCE: 22
cgctggatat ctacatgcac gtatttattg ccattccg                                   38

<210> SEQ ID NO 23
<211> LENGTH: 74
<212> TYPE: DNA
<213> ORGANISM: Artificial sequence
<220> FEATURE:
<223> OTHER INFORMATION: PCR primer

<400> SEQUENCE: 23
tacgggatcc accagaacca ccagaaccac cagaaccacc agaaccacct gctacataat           60
ccgaggctct aaag                                                             74

<210> SEQ ID NO 24
<211> LENGTH: 108
<212> TYPE: DNA
<213> ORGANISM: Artificial sequence
<220> FEATURE:
<223> OTHER INFORMATION: PgsA6

<400> SEQUENCE: 24
cacgtattta ttgccattcc gatcgttttt gtccttatgt tcgctttcat gtgggcggga           60
aaagcggaaa cgccgaaggt caaaacgtat tctgacgacg tactctca                       108

<210> SEQ ID NO 25
<211> LENGTH: 138
<212> TYPE: DNA
<213> ORGANISM: Artificial sequence
<220> FEATURE:
<223> OTHER INFORMATION: PgsA7

<400> SEQUENCE: 25
cacgtattta ttgccattcc gatcgttttt gtccttatgt tcgctttcat gtgggcggga           60
aaagcggaaa cgccgaaggt caaaacgtat tctgacgacg tactctcagc ctcatttgta          120
ggcgatatta tgatggga                                                        138

<210> SEQ ID NO 26
<211> LENGTH: 228
<212> TYPE: DNA
<213> ORGANISM: Artificial sequence
<220> FEATURE:
<223> OTHER INFORMATION: PgsA8

<400> SEQUENCE: 26
cacgtattta ttgccattcc gatcgttttt gtccttatgt tcgctttcat gtgggcggga           60
aaagcggaaa cgccgaaggt caaaacgtat tctgacgacg tactctcagc ctcatttgta          120
ggcgatatta tgatgggacg ctatgttgaa aaagtaacgg agcaaaaagg ggcagacagt          180 attttttcaat atgttgaacc gatctttaga gcctcggatt atgtagca                      228
```

SURFACE EXPRESSION VECTOR USING POLY-GAMMA-GLUTAMATE SYNTHETIC GENE DERIVED FROM STRAIN IN *BACILLUS*, AND METHOD FOR EXPRESSING PROTEIN ON SURFACE OF MICROORGANISM, USING SAME

CROSS-REFERENCE TO RELATED APPLICATIONS

The present application is a U.S. national-stage application of International Application No. PCT/KR2019/007592 filed on Jun. 24, 2019, which claims priority to/from and the benefit of Korean Application No. 10-2018-0073345 filed on Jun. 26, 2018, both of which are incorporated herein by reference in their entirety.

SEQUENCE LISTING

The present application contains a Sequence Listing which has been submitted electronically in ASCII format and is incorporated herein by reference in its entirety. Said ASCII copy, created on Jul. 26, 2021, is named "8SI8356.TXT" and is 8,192 bytes in size. The Sequence Listing does not go beyond the disclosure of this application as filed.

TECHNICAL FIELD

The present invention relates to a novel vector which expresses a foreign protein on the microbial surface using an outer-membrane protein (pgsA), which is derived from a *Bacillus* sp. strain and involved in the synthesis of poly-gamma-glutamate. Moreover, the present invention relates to a method of producing a protein by expressing a foreign protein on the microbial surface using an outer-membrane protein, which is derived from a *Bacillus* sp. strain and involved in the synthesis of poly-gamma-glutamate.

BACKGROUND ART

Cell surface display refers to a technique in which a protein or a peptide is fused with an appropriate anchoring motif and expressed on the surface of gram-negative or positive bacteria, fungi, yeast, or animal cells (Lee S. Y., et al., Trends Biotechnol., 21:4552, 2003). According to the first cell surface display technique developed in the 1980s, a peptide or a small protein is fused with pIII of the filamentous phage using a phage having a relatively simple surface and is expressed on the phage surface. Thus, the cell surface display technique was named surface-expression system. Cell surface display using a phage was used in antibody screening of antibodies or screening of epitopes, high-affinity ligands and the like, but had a limitation in that the size of a protein that may be expressed on the phage surface is relatively limited. Therefore, as an alternative thereto, cell surface expression using bacteria has been developed. This is a field in which a foreign protein is stably expressed on the microbial surface using a surface protein of a microorganism such as a bacterium or fungus as a surface anchoring motif.

In order to express a foreign protein on the cell surface using an outer-membrane protein of a specific organism, a fusion protein should be biosynthesized by connecting a suitable surface protein and the foreign protein to each other at the gene level and they should stably pass through the inner membrane and should remain anchored to the cell surface. To this end, it is preferable to use a protein having the following properties as a surface anchoring motif: First, the protein should have, at its N-terminus, a secretion signal capable of passing through the inner membrane; second, the protein should have a targeting signal that can be stably anchored to the outer membrane surface; third, the protein should be expressed in large amounts on the cell surface within a range that does not adversely affect the growth of the cell so that the protein can exhibit high activity; and finally, the protein should be expressed stably regardless of the size thereof so that it can be used for various reactions (Georgiou et al., TIBTECH, 11:6, 1993). This surface anchoring motif needs to be genetically engineered to be inserted at the N-terminus or C-terminus of the outer-membrane protein on the surface of a host cell or inserted into the center of the protein (Lee et al., TIBTECH, 21:45, 2003).

In order for a protein to be expressed on the bacterial surface, a secretion signal enabling the protein biosynthesized in the cell to pass through the cell membrane should be located on the primary sequence of the protein. In addition, in the case of Gram-negative bacteria, the protein should pass through the inner membrane and the periplasmic space and should be inserted into and anchored to the outer membrane so as to protrude from the membrane.

In the case of bacteria, examples of proteins having this secretion signal and a targeting signal that can be stably anchored to the cell surface include surface proteins, special enzymes, toxin proteins, and the like. In fact, if the secretion signal and targeting signal of these proteins are used together with an appropriate promoter, the protein can be successfully expressed on the bacterial surface.

Bacterial surface proteins that are used for surface expression of foreign proteins can be broadly divided into four types: cell outer-membrane proteins, lipoproteins, secretory proteins, and cell surface proteins. To date. attempts have been made to express necessary foreign proteins on the bacterial surface using surface proteins present mainly in Gram-negative bacteria, for example, LamB, PhoE, OmpA, and the like. When these proteins are used, the foreign protein is inserted into a protruding loop on the cell surface, and thus the size of the protein that can be structurally inserted is limited. In addition, since the C-terminus and the N-terminus of the foreign protein to be inserted should be located sterically close to each other, a problem arises in that, when the distance between the C-terminus and the N-terminus is long, the two termini should be brought close to each other by a linker peptide.

In fact, when a foreign polypeptide consisting of 50 to 60 or more amino acids or more was inserted using LamB or PhoE, a stable amino acid was not formed due to structural limitations [Charbit et al., J. Immunol., 139: 1658-1664 (1987); Agterberg et al., Vaccine, 8: 85-91 (1990)]. Although there was also a case in which a foreign protein was inserted into a protruding loop using OmpA, only an OmpA fragment containing a minimal targeting signal capable of being anchored to the outer membrane was used in order to overcome structural limitations. As this method, there is a case in which bata-lactamase is linked to the C-terminus of the OmpA targeting signal and expressed on the cell surface.

In addition, in recent years, surface expression using an ice-nucleation protein (INP) derived from *Pseudomonas* sp. as an outer membrane protein of a Gram-negative bacterium was attempted [Jung et al., Nat, Biotechnol, 16: 576-560 (1998), Jung et al., Enzyme Microb. Technol, 22(5): 348-354 (1998), Lee et al., Nat. Biotechnol, 18: 645-648 (2000)]. Jung et al. fused levansucrase to the C-terminus of an ice-nucleation protein, which consists of an N-terminus, a central repeating region and the C-terminus, and carboxymethylcellulase to the C-terminus of an ice-nucleation protein, from which the central repeating region was deleted and which consists of an N-terminus and the C-terminus, subjected each enzyme to surface expression, and analyzed the activity of each enzyme. Also, Lee et al. fused to hepatitis B virus surface antigen and hepatitis C virus core antigen to each terminus of an ice-nucleation protein consisting of either an N-terminus or an N-terminus and a C-terminus, expressed these antigens on the surface of a *Salmonella typhi* Ty21a strain, and then confirmed that these antigens may be used as complex live vaccine.

Lipoproteins are also surface proteins that are used for surface expression. In particular, *E. coli* lipoprotein has a secretion signal at the N-terminus and can pass through the inner membrane, and L-cysteine at the terminus thereof is covalently attached directly to an outer-membrane lipid or an inner-membrane lipid. The main lipoprotein Lpp is bound to the outer membrane at the N-terminus and to the cell membrane (peptidoglycan (PG)) at the C-terminus, and thus when it is linked to the outer-membrane protein OmpA fragment, a foreign protein may be secreted to the outer membrane and surface-expressed [Francisco et al., Proc. Natl. Acad. Sci. USA, 489: 2713-2717 (1992)]. Another lipoprotein, TraT, was used to surface-express a peptide such as the C3 epitope of poliovirus using this property of the lipoprotein [Felici et al., J. Mol. Biol., 222: 301-310 (1991)]. In addition, a peptidoglycan-associated lipoprotein (PAL), whose exact function is not yet known, was also used for surface expression of a recombinant antibody [Fuchs et al., Bio/Technology, 9: 1369-1372(1991)]. In this case, the C-terminus of the PAL was linked to the cell wall and the N-terminus thereof was linked to a recombinant antibody, whereby a fusion protein was surface expressed.

Secretory proteins that pass through the outer membrane may also be used as surface proteins. However, in the case of Gram-negative bacteria, secretory proteins are not developed, and only for some secretory proteins, proteins that are involved in the peculiar secretory mechanism of the secretory proteins exist and help the secretory proteins to pass through the outer membrane. For example, *Klebsiella* sp. pullulanase is a lipoprotein whose N-terminus is anchored to the outer membrane by being replaced with a lipid, and is then completely secreted into a cell culture medium. Kornacker et al. expressed beta-lactamase on the cell surface using the N-terminal fragment of pullulanase, but there was a disadvantage in that the expressed pullulanase/beta-lactamase fusion protein is temporarily anchored to the cell surface, and is then released into the cell culture medium. In addition, when the periplasmic space alkaline phosphatase was expressed using N-terminal fragment of pullulanase, it was not stably surface-expressed because at least 14 proteins are involved in secretion of the alkaline phosphatase [Kornacker et al., Mol. Microl., 4: 1101-1109 (1990)].

IgA protease derived from the pathogenic microorganism *Neisseria* having a unique secretion system has a signal that allows the fragment at the C-terminus and the protease at the N-terminus to be anchored to the outer membrane. Once the protease reaches the outer membrane and protrudes from the cell surface, it is secreted into the cell culture medium by its hydrolysis ability. Krauser et al. stably expressed an about 12-kDa cholera toxin B subunit on the cell surface using this IgA protease fragment [Klauser et al., EMBO J., 9:1991-1999 (1990)]. However, secretion of the fusion protein was inhibited by protein folding that occurred in the periplasmic space during the secretion process.

In addition, in the case of Gram-negative bacteria, cell organelles, which are present on the cell surface and may be applied to surface expression, include flagella, pili, and fimbriae. A cholera toxin B subunit and a peptide derived from hepatitis B virus were stably expressed using flagella protein (Flagellin), which is the constituent subunit of flagella, and they reacted strongly with antibodies against them [Newton et al., Science, 244: 70-72 (1989)]. As a result of attempting to express foreign peptides on the cell surface using fimbrilin, a constituent protein of fimbriae that looks like a thread, only small peptides were successfully expressed [Hedegaard et al., Gene, 85:115-124 (1989)].

In addition to surface expression attempted using surface proteins of Gram-negative bacteria as described above, surface expression using surface proteins of Gram-positive bacteria has been recently attempted [Samuelson et al., J. Bacteriol., 177:1470-1476 (1995)]. Even in this case, a secretion signal, which is capable of passing through the inner membrane, and a surface anchoring motif which is anchored to the cell membrane, are required. In fact, there was a case in which a malaria blood stage antigen consisting of 80 amino acids and an albumin adhesion protein derived from *Streptococcus* protein G were effectively expressed on the surface of Gram-positive bacteria using *Staphylococcus hyicus* lipase as a secretion signal and *Staphylococcus aureus* protein A as a membrane-anchoring motif.

Many useful protein expression systems have been developed through the above-described studies on expression on the surfaces of Gram-negative and Gram-positive bacteria, and have been applied for patent protection in the United States, Europe, Japan, and the like. Among them, in particular, five cases (WO9504069, WO9324636, WO9310214, EP603672, and U.S. Pat. No. 5,356,797) were found regarding the use of outer-membrane proteins of Gram-negative bacteria, and one case (WO9410330) was found regarding the use of the cell surface organelle pili, and one case (WO9504079) was found regarding the use of cell surface lipoproteins.

In order to express a foreign protein on the cell surface using a bacterial outer-membrane protein as described above, an appropriate outer-membrane protein and the foreign protein should be linked together at the gene level to induce biosynthesis of a fusion protein, and they should stably pass through the inner membrane and should remain anchored to the outer membrane. However, a surface-anchoring motif that satisfies all of the above conditions has not yet been developed, and so far is a level that remedying the disadvantages of the above-described cases.

Under this background, the present inventors have conducted studies on the use of a poly-gamma-glutamate synthetase gene (pgsA) derived from a *Bacillus* sp. strain as a new surface-anchoring motif, and as a result, have developed a new vector that effectively expresses a foreign protein on the microbial surface using the pgsA gene, and a method of expressing a large amount of a foreign protein on the microbial surface, thereby completing the present invention.

DISCLOSURE

Technical Problem

An object of the present invention is to select, as a surface-anchoring motif capable of expressing a large amount of a foreign protein on the microbial surface, an outer-membrane protein which is derived from a *Bacillus* sp. strain and involved in the synthesis of poly-gamma-glutamate, construct a surface expression vector for expression of a target protein, which is capable of expressing a foreign protein or peptide on the microbial surface using the surface-anchoring motif, and provide a method of efficiently expressing a foreign protein on the surfaces of various transformants transformed with the surface expression vector.

Technical Solution

To achieve the above object, the present invention provides a surface expression vector for expression of a target protein, the surface expression vector comprising: the gene pgsA encoding a poly-gamma-glutamate synthetase complex; and a gene encoding the target protein, wherein the gene pgsA encoding the poly-gamma-glutamate synthetase complex has the nucleotide sequence of any one of SEQ ID NOs: 13 to 16 and 24 to 26.

In the present invention, the gene pgsA may be derived from a *Bacillus* sp. strain that produces poly-gamma-glutamate.

In the present invention, the gene pgsA encoding the poly-gamma-glutamate synthetase complex may have the nucleotide sequence of SEQ ID NO: 17.

In the present invention, a linker may be inserted at a terminal end of the gene pgsA, and the gene encoding the target protein is inserted into the inserted linker.

In the present invention, a portion of the amino acid sequence of the target protein may be removed or site-specifically mutated to favor surface expression of the target protein.

In the present invention, the nucleotide sequence may comprise an aldolase promoter derived from lactic acid bacteria.

In the present invention, the nucleotide sequence may comprise an aldolase promoter derived from lactic acid bacteria.

The present invention also provides a microorganism transformed with the surface expression vector.

In the present invention, a microorganism which is used to obtain the transformed microorganism may be a microorganism modified to favor cell-surface expression of the target protein so that it does not produce intracellular or extracellular proteases that are involved in degradation of the expressed target protein.

In the present invention, the microorganism may be lactic acid bacteria.

In the present invention, the microorganism that is used as the host may be lactic acid bacteria. The lactic acid bacteria may include *Lactobacillus* sp., *Streptococcus* sp., and *Bifidobacterium* sp. Typically, the *Lactobacillus* sp. includes *L. acidophilus, L. casei, L. plantarum, L. ferementum, L. delbrueckii, L. johnsonii* LJI, *L. reuteri* and *L. bulgaricus*; the *Streptococcus* sp. includes *S. thermophilus*; and the *Bifidobacterium* sp. includes *B. infantis, B. bifidum, B. longum, B. psuedolongum, B. breve, B. lactis* Bb-12 and *B. adolescentis*. More preferably, the microorganism is *Lactobacillus* sp.

The present invention also provides a method for cell surface expression of a target protein, the method comprising steps of: expressing the target protein on a cell surface by culturing the transformed microorganism; and recovering cells having the target protein expressed on the surface thereof.

In the present invention, the target protein may be any one selected from the group consisting of a hormone, a hormone analogue, an enzyme, an enzyme inhibitor, a signaling protein or a portion thereof, an antibody or a portion thereof, a single-chain antibody, a binding protein, a binding domain, a peptide, an antigen, an adhesion protein, a structural protein, a regulatory protein, a toxin protein, a cytokine, a transcription regulatory factor, a blood coagulation factors, and a plant defense-inducing protein.

The present invention also a method of inducing humoral immunity or cell-mediated immunity by administering cells, which are produced by the above method and have an antigen expressed on the surface thereof, to vertebrate animals except humans.

In the present invention, the vector may be applied to Gram-negative bacteria or Gram-positive bacteria.

The present invention also provides a method of expressing a target protein on a surface of a Gram-negative or Gram-positive host cell, the method comprising steps of: (a) constructing a recombinant vector by inserting a gene encoding a target protein into the above-described surface expression vector; (b) transforming the Gram-negative or Gram-positive host cell with the recombinant vector; and (c) expressing the target protein on the surface of the host cell by culturing the transformed host cell.

Advantageous Effects

The surface expression vector for expression of a target protein according to the present invention may stably express the target protein. In addition, the surface expression vector according to the present invention may constitutively express the target protein and, at the same time, may be effectively used to produce a necessary antigen for vaccine production by expression on the surface of a recombinant microorganism.

BEST MODE

Figure 1:
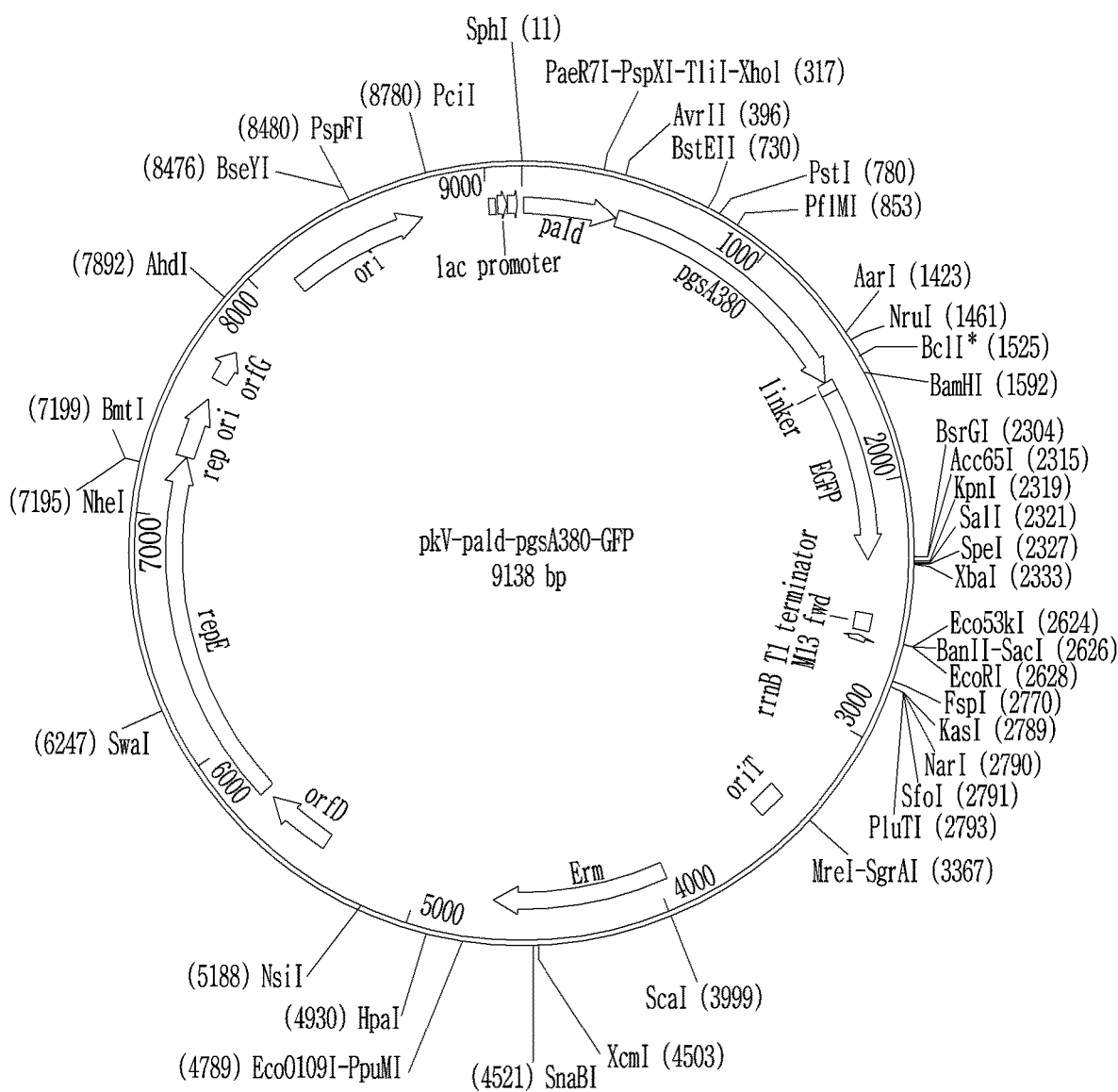
FIG. 1 shows a genetic map of the surface expression vector pKV-Pald-PgsA-EGFP according to the present invention, which uses *Lactobacillus casei* as a host.
Figure 2:
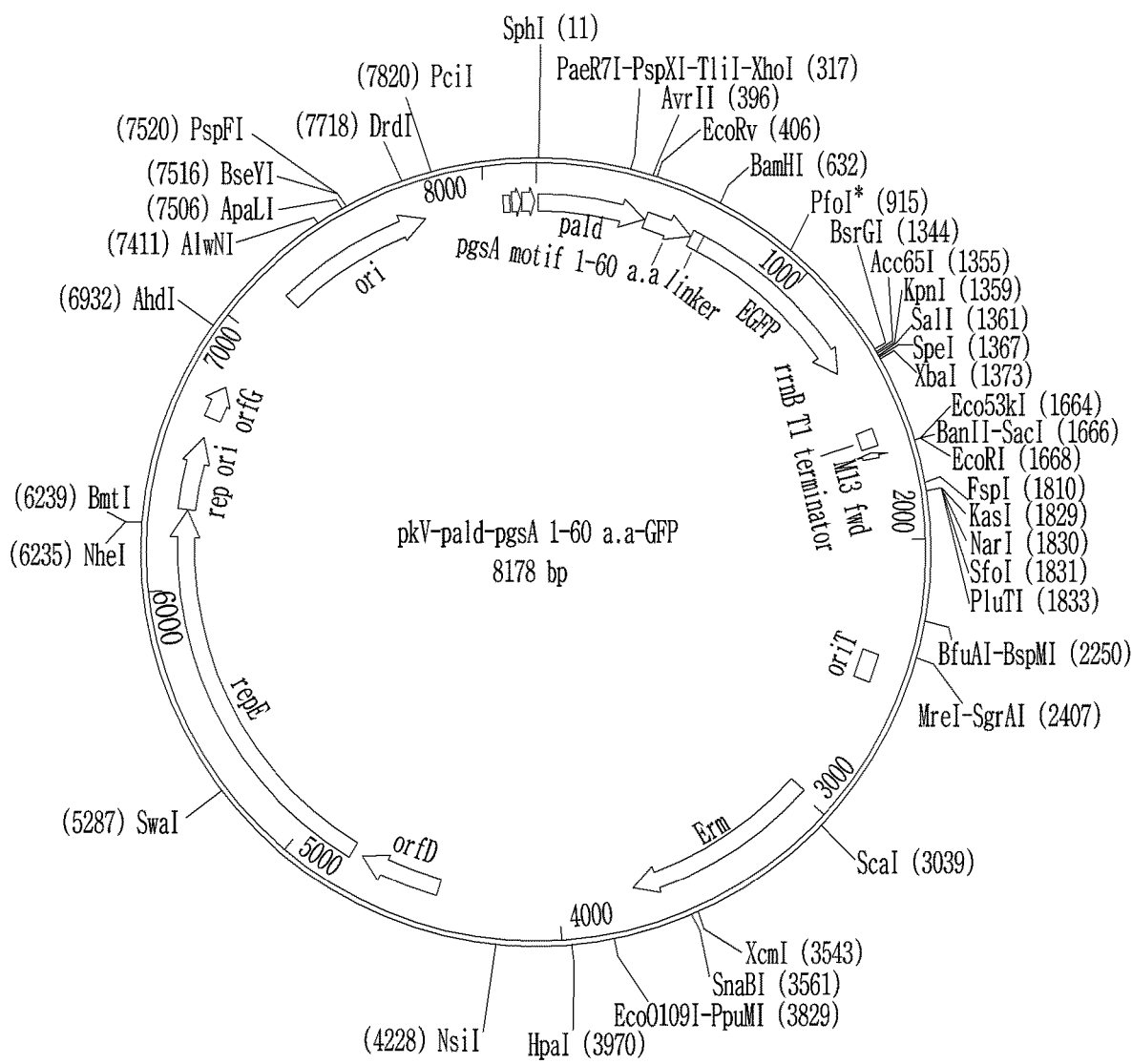
FIG. 2 shows a genetic map of the surface expression vector pKV-Pald-pgsA1 (PgsA motif 1-60 a.a-EGFP) according to the present invention, which uses *Lactobacillus casei* as a host.
Figure 3:
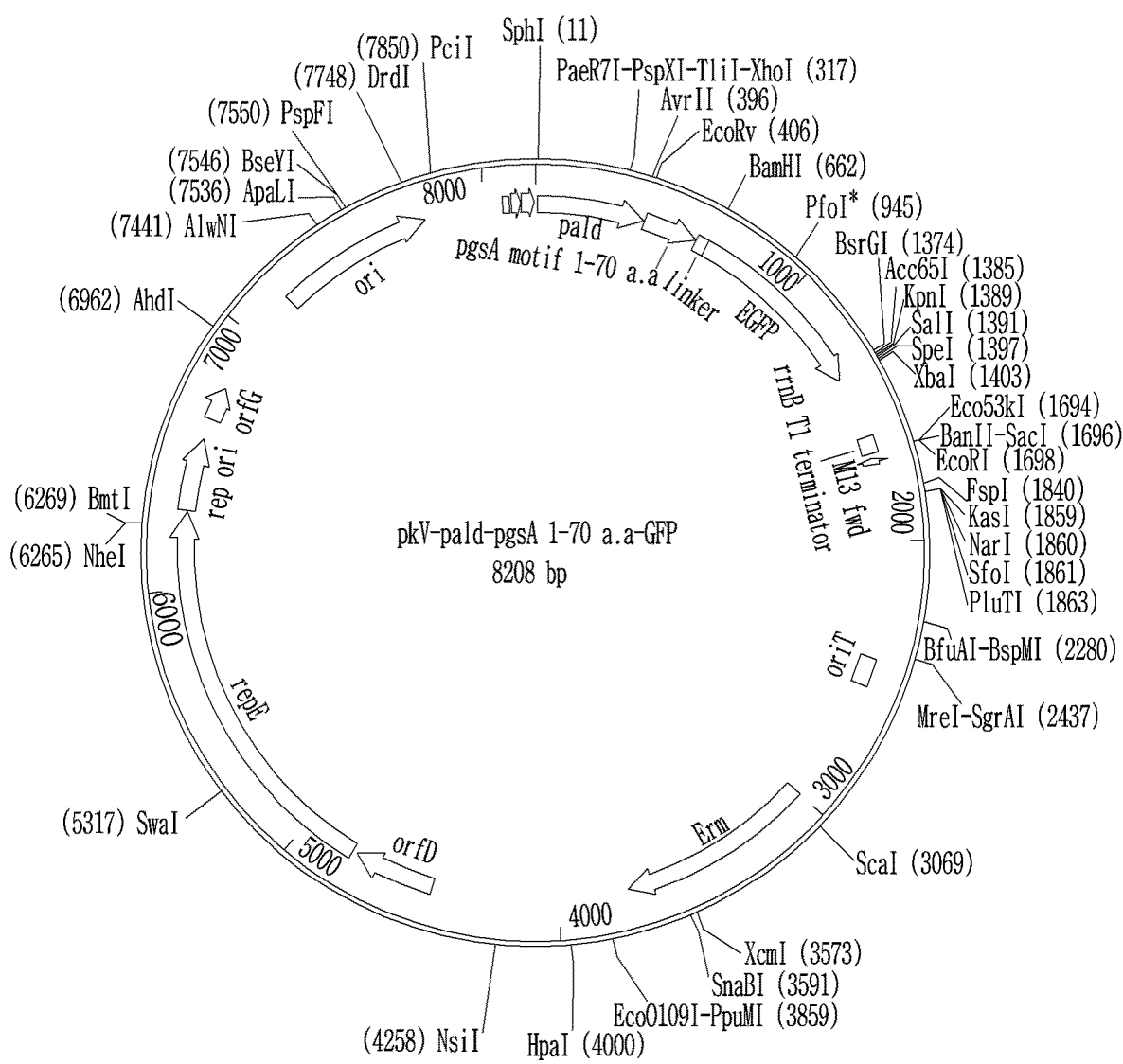
FIG. 3 shows a genetic map of the surface expression vector pKV-Pald-pgsA2 (PgsA motif 1-70 a.a-EGFP) according to the present invention, which uses *Lactobacillus casei* as a host.
Figure 4:
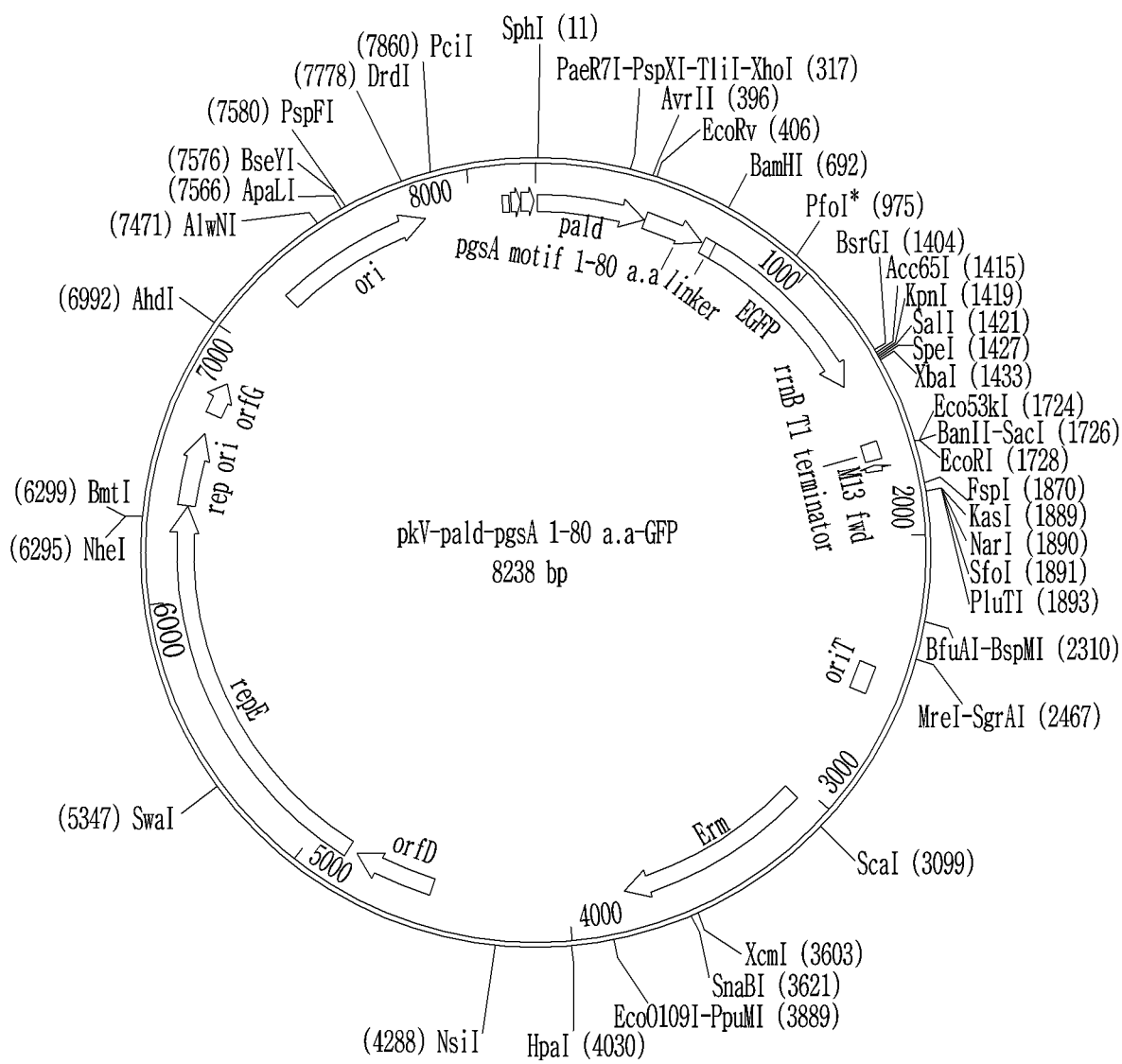
FIG. 4 shows a genetic map of the surface expression vector pKV-Pald-pgsA3 (PgsA motif 1-80 a.a-EGFP) according to the present invention, which uses *Lactobacillus casei* as a host.
Figure 5:
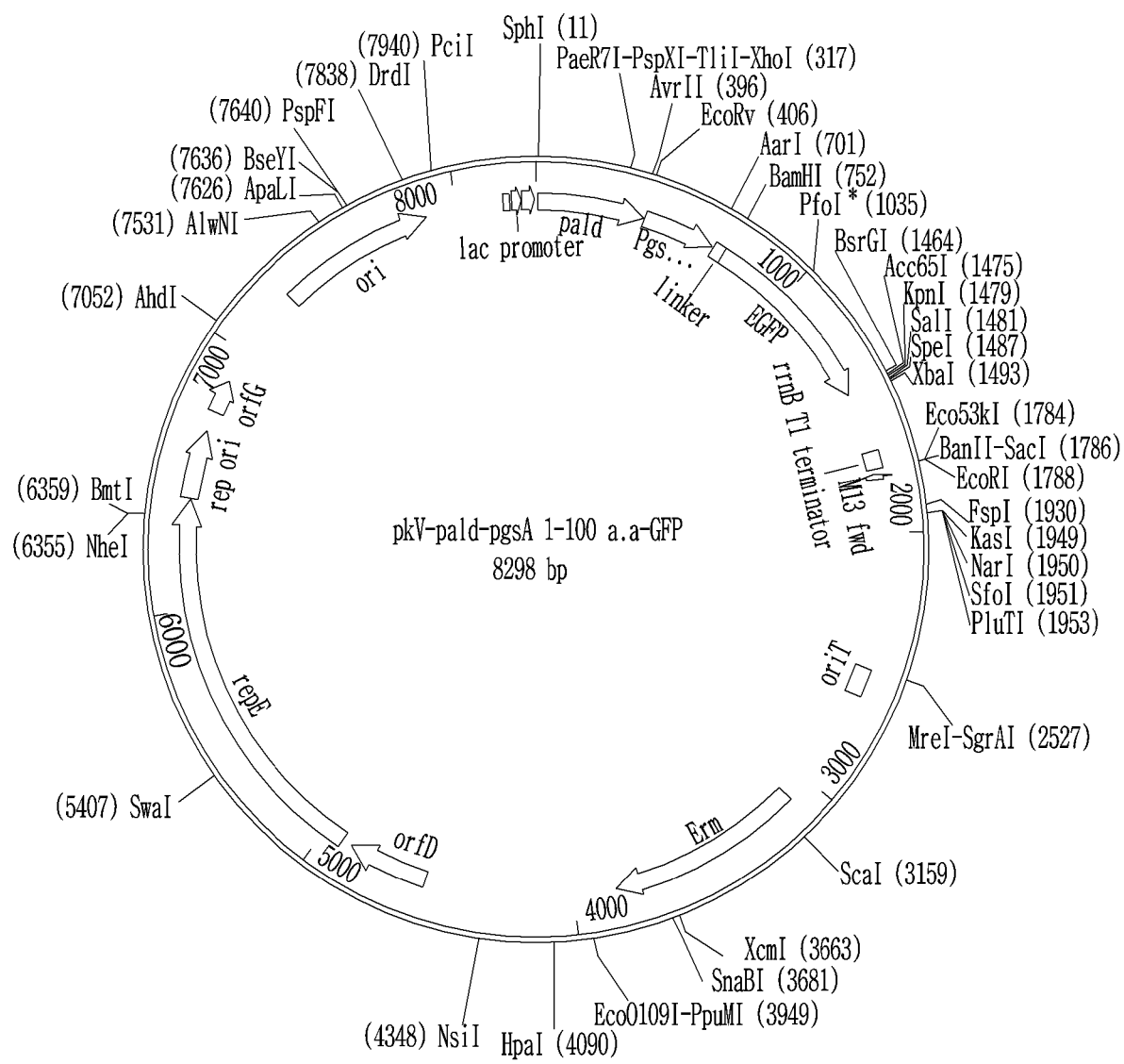
FIG. 5 shows a genetic map of the surface expression vector pKV-Pald-pgsA5 (PgsA motif 1-100 a.a-EGFP) according to the present invention, which uses *Lactobacillus casei* as a host.
Figure 6:
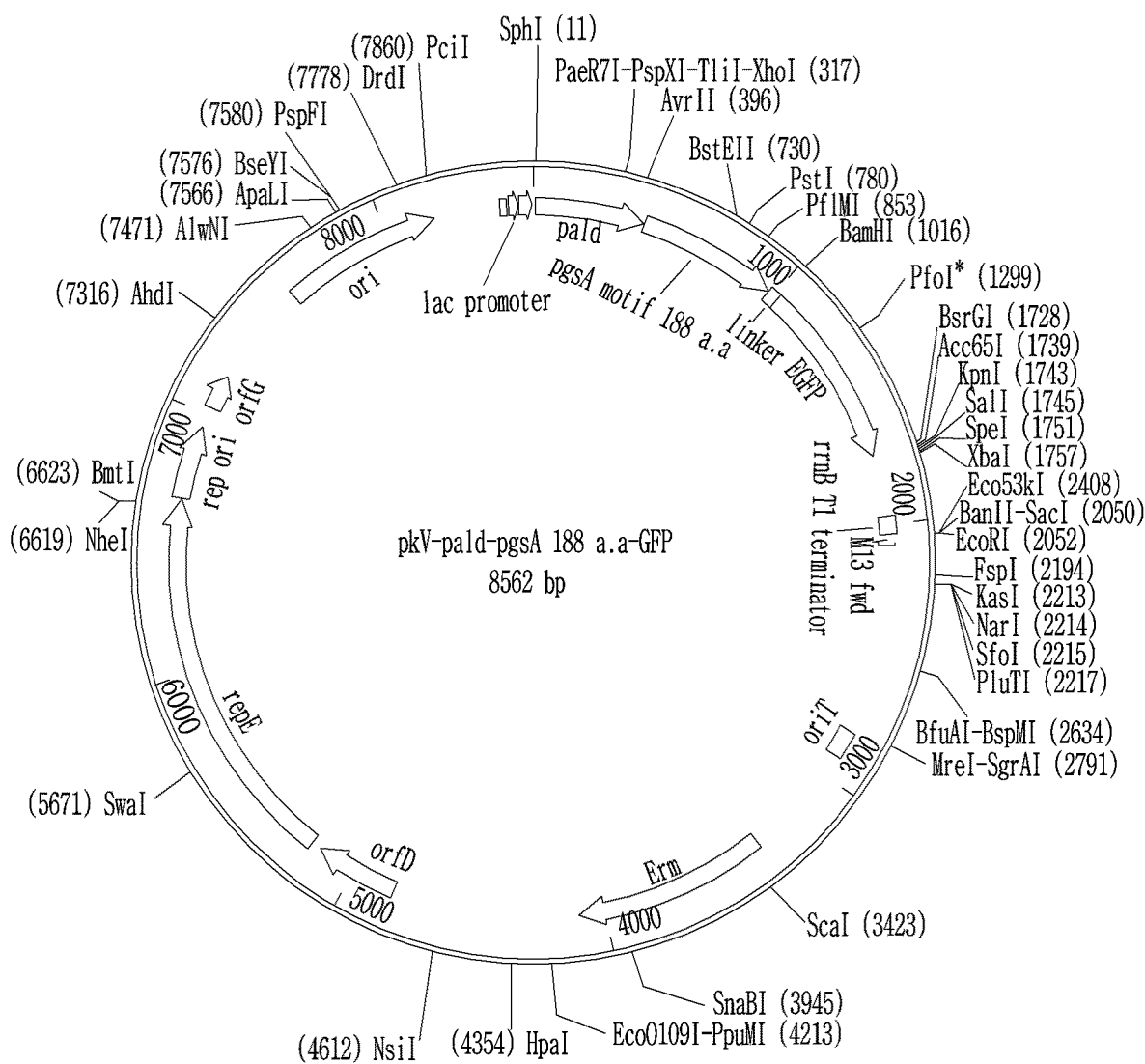
FIG. 6 shows a genetic map of the surface expression vector pKV-Pald-pgsA5 (pKV-PgsA 1-188 a.a-EGFP) according to the present invention, which uses *Lactobacillus casei* as a host.

Improvement of the surface expression vector (pKV-Pald-PgsA-EGFP) constructed in Example 1 was performed to obtain PgsA gene fragments capable of more stably exhibiting a high expression rate in a lactic acid bacterium host.

First, to obtain PgsA fragments containing each of 1-60 a.a, 1-70 a.a, 1-80 a.a, 1-100 a.a and 1-188 a.a among PgsA fragments, PCR was performed using a surface expression vector (pKV-Pald-PgsA-EGFP) as a template and primers of SEQ ID NOs: 3 to 12.

As a result, DNA fragments were obtained, which contained an aldolase promoter and contained the respective PgsA motif fragments. Each of the DNA fragments contained a SphI restriction enzyme site at the 5' end and a BamHI restriction enzyme site at the 3' end. The obtained DNA fragments were treated with SphI and BamHI. In addition, it was confirmed that the PgsA1 to PgsA5 motif fragments had the nucleotide sequences of SEQ ID NOs: 13 to 17, respectively.

Meanwhile, to obtain PgsA fragments containing 25-60 a.a, 25-70 a.a and 25-100 a.a among PgsA fragments, PCR was performed using the surface expression vector (pKV-Pald-PgsA-EGFP) as a template and primers of SEQ ID NOs: 18 to 23.

As a result, DNA fragments containing the respective PgsA motif fragments were obtained. Each of the DNA fragments contained an EcoRV restriction enzyme site at the 5' end and a BamHI restriction enzyme site at the 3' end. The obtained DNA fragments were treated with EcoRV and BamHI to obtain fragments. In addition, it was confirmed that the PgsA motif fragments had the nucleotide sequences of SEQ ID NOs: 24 to 26, respectively.

Mode for Invention

An object of the present invention is to select, as a surface-anchoring motif capable of expressing a large amount of a foreign protein on the microbial surface, an outer-membrane protein which is derived from a *Bacillus* sp. strain and involved in the synthesis of poly-gamma-glutamate, construct a surface expression vector for expression of a target protein, which is capable of expressing a foreign protein or peptide on the microbial surface using the surface-anchoring motif, and provide a method of efficiently expressing a foreign protein on the surfaces of various transformants transformed with the surface expression vector.

To achieve the above object, the present invention provides a microbial surface expression vector, which comprises the gene pgsA encoding a poly-gamma-glutamate synthetase complex, and a strain transformed with the vector.

To the above object, the present invention also provides a method of expressing a foreign protein on the surface of the transformed strain using the microbial surface expression vector.

A protein that is encoded by the gene pgsA is an outer-membrane protein present in *Bacillus* sp., and is a protein which is involved in the synthesis of poly-gamma-glutamic acid that is an edible, water-soluble, anionic, and biodegradable polymer from *Bacillus subtilis* IFO3336 (*Bacillus natto*; Biochem. Biophy. Research Comm., 263, 6-12, 1999), *Bacillus licheniformis* ATCC9945 (Biotech. Bioeng. 57(4), 430-437, 1998), *Bacillus anthracis* (J. Bacteriology, 171, 722-730, 1989), and the like.

In the case of *Bacillus subtilis* IFO3336, an outer-membrane protein isolated from the bacterial is a protein consisting of a total of 922 amino acids, and consists of pgsB, pgsC and pgsA. Here, pgsB consists of 393 amino acids, pgsC consists of 149 amino acids, and pgsA consists of 380 amino acids. Ashiuchi et al. cloned a poly-gamma-glutamate synthetase gene derived from *Bacillus subtilis* IFO3336, transformed the gene into *E. coli*, and observed the synthesis of poly-gamma-glutamate in the *E. coli* [Ashiuchi et al., Biochem. Biophy. Res. Communications, 263: 6-12 (1999)].

However, the specific role and function of the protein pgsA encoding the poly-gamma-glutamate synthetase complex has not yet been identified. Among the constituent proteins of the complex, pgsB belongs to the amide ligase family, specific amino acids at the N-terminus of pgsB interact with the cell membrane or wall, and pgsA has hydrophilic specific amino acid sequences at the N-terminus and the C-terminus. Thus, it is assumed that pgsA has a secretion signal, a targeting signal and an anchoring signal, which allow these amino acid sequences to pass through the inner membrane with the help of pgsB.

As a result of studies conducted by the present inventors, it has been found that the outer-membrane protein which is involved in the synthesis of poly-gamma-glutamate has many advantages as a surface-anchoring motif that expresses a foreign protein on the cell surface due to the amino acid primary sequence structure and characteristics thereof. First, the outer-membrane protein which is involved in the synthesis of poly-gamma-glutamate may be expressed in large amounts on the cell surface for the synthesis and extracellular secretion of poly-gamma-glutamate. Second, the expressed outer-membrane protein which is involved in the synthesis of poly-gamma-glutamate remains stable even in the resting phase of the cell cycle. Third, structurally, in particular pgsA protrudes from the cell surface. Fourth, the outer-membrane protein which is involved in the synthesis of poly-gamma-glutamate has advantages in that it originates from the surface of Gram-positive bacteria and may be stably expressed on the surfaces of various Gram-positive bacteria or Gram-negative bacteria.

An object of the present invention is to provide a useful vector capable of expressing a foreign protein on the bacterial surface using the characteristics of the outer-membrane protein which is involved in the synthesis of poly-gamma-glutamate. In particular, the surface expression vector for expression of a target protein according to the present invention comprise a secretion signal and a targeting signal, which are derived from the primary sequence of the outer-membrane protein which is involved in the synthesis of poly-gamma-glutamate.

Another object of the present invention is to provide a method of expressing a foreign protein on the bacterial surface using the surface expression vector based on the characteristics of the outer-membrane protein which is involved in the synthesis of poly-gamma-glutamate. In particular, the present invention provides a method for producing a foreign protein, which enables the foreign protein to be efficiently used without a cell lysis process or a protein isolation/purification process, by expressing the foreign protein on the microbial surface using the outer-membrane protein which is involved in the synthesis of poly-gamma-glutamate.

As used herein, the term "target protein" or "foreign protein" refers to a protein that cannot normally exist in a transformed host cell expressing the protein. For example, when lactic acid bacteria are artificially engineered to express a virus-derived or tumor-derived protein, the protein is referred to as a foreign protein or a target protein.

More specifically, preferred examples of the target protein include, but are not limited to, antigen derived from infectious microorganisms, antigens derived from immune diseases, or tumor-derived antigens, for example, antigens derived from fungal pathogens, bacteria, parasites, intestinal parasites, viruses or allergens. More specifically, examples of the antigens include tetanus toxoid, influenza virus hemagglutinin or nucleoprotein, diphtheria toxoid, HIV gp120 or a fragment thereof, HIV gag protein, IgA protease, insulin peptide B, *Spongospora subterranea* antigen, vibriose antigens, *Salmonella* antigens, Pneumococcus antigens, RSV (respiratory syncytial virus) antigens, *Hemophilus influenza* outer membrane proteins, *Streptococcus pneumoniae* antigens, *Helicobacter pylori* urease, *Neisseria meningitidis* pilins, *N. gonorrhoeae* pilins, melanoma associated antigens (TRP2, MAGE-1, MAGE-3, gp100, tyrosinase, MART-1, HSP-70, beta-HCG), human papilloma virus antigens including E1, E2, E6 and E7 from HPV-16, -18, -31, -35 or -45, CEA tumor antigen, normal or mutant ras protein, normal or mutant p53, Muc1, pSA, as well as antigens well known in the art, which are derived from cholera, diphtheria, *Haemophilus*, hepatitis A, hepatitis B, influenza, measles, meningitis, mumps, pertussis, small pox, pneumococcal pneumonia, polio, rabies, rubella, tetanus, tuberculosis, Addison's disease, immunogens, allergens, cancers including solid and blood borne tumors, acquired immune deficiency syndrome, and factors that are involved in transplant rejections, such as kidney, heart, pancreas, lung, bone, and liver transplant rejections, and antigens inducing autoimmunity.

Therefore, the foreign protein produced by the surface expression method of the present invention may be applied for various applications. Such applications include the effective production of antibodies and enzymes, as well as the production of peptide libraries for screening antigens, adhesion or adsorption proteins and new physiologically active substances.

Surface expression vectors comprising genes which are involved in the synthesis of all types of poly-gamma-glutamate, including outer-membrane proteins which derived from *Bacillus* sp. strains and involved in the synthesis of poly-gamma-glutamate, are all included within the scope of the present invention.

In addition, the surface expression vector comprising the poly-gamma-glutamate synthetase gene according to the present invention may be applied to all strains in order to express a foreign protein on the microbial surface.

Preferably, the surface expression vector may be applied to Gram-negative bacteria, more preferably *E. coli, Salmonella typhi, Salmonella typhimurium, Vibrio cholera, Mycobacterium bovis, Shigella*, and Gram-positive bacteria, preferably *Bacillus, Lactobacillus, Lactococcus, Staphylococcus, Listeria monocytogenes*, and *Stratococcus* strains. All methods of producing foreign proteins using the above strains are included within the scope of the present invention.

If necessary, various recognition sites of all or some restriction enzymes may be inserted into the N-terminus or C-terminus of the poly-gamma-glutamate synthetase gene. Surface expression vectors in which these restriction enzyme sites are inserted are all included within the scope of the present invention.

Specifically, the present invention provides the surface expression vectors pKV-Pald-pgsA1 to pKV-Pald-pgsA8, which comprise the poly-gamma-glutamate synthetase gene pgsA derived from a *Bacillus* sp. strain and into which various foreign genes may be cloned by cloning a restriction enzyme recognition site into the C-terminus of pgsA.

The present invention provides the surface expression vectors pKV-Pald-pgsA1 to pKV-Pald-pgsA8, which comprise the outer-membrane protein complex pgsA among outer-membrane protein complexes involved in the synthesis of poly-gamma-glutamate and may express EGFP protein in the form of a fusion protein on the surface of Gram-positive bacteria by linking the N-terminus of the EGFP protein to the C-terminus of pgsA.

In particular, in one example of the present invention, the outer-membrane protein gene pgsA involved in the synthesis of poly-gamma-glutamate was obtained from *Bacillus subtilis* var. *chungkookjang* (KCTC 0697BP). However, either constructing a vector using the pgsA gene derived from any *Bacillus* sp. strain that produces poly-gamma-glutamate or surface-expressing a foreign gene using the vector will also be included within the present invention. For example, either constructing a vector using the pgsA gene derived from other strains, which has a homology of 80% or more to the nucleotide sequence of the pgsA gene present in *Bacillus subtilis* var. *chungkookjang*, or surface-expressing a foreign protein using the vector will also be included in the scope of the present invention.

In another example of the present invention, in order to examine whether a protein is effectively expressed on the surface of *E. coli* cells, enhanced green fluorescent protein (EGFP) was selected from a model protein. The "EGFP (enhanced green fluorescent protein) gene" is a gene that makes it easy to observe a cell expressing the protein of interest by emitting green light in vivo, and has an advantage in that it may be observed under a fluorescence microscope. GFP is a green fluorescent protein originating from jellyfish (*Aequorea victoria*) and has been used as an important marker of gene expression in various research fields. EGFP is a mutant of GFP wherein the amino acid phenylalanine at position 64 of the original GFP is replaced with leucine and the amino acid serine at position 65 is replaced with threonine. Thus, EGFP has the advantage of emitting a stronger fluorescence signal than the original GFP.

The present inventors obtained proteins by inserting the EGFP gene into the constructed recombinant vectors pKV-Pald-pgsA1 to pKV-Pald-pgsA8 to construct surface expression vectors, transforming *Lactobacillus casei* with each of the constructed surface expression vectors, inducing expression by culture, and collecting certain amounts of the culture media. The obtained proteins were analyzed by SDS-PAGE and subjected to Western blotting using anti-EGFP antibody. As a result, it was confirmed that the protein EGFP was successfully inserted into the constructed recombinant vectors pKV-Pald-pgsA1 to pKV-Pald-pgsA8 and was expressed on the cell surface.

In addition, although the EGFP protein was used as the foreign protein in the example, any proteins such as other enzymes, antigens, antibodies, adhesion proteins may be used as foreign proteins.

In addition, in the following examples, surface expression vectors that are applied to Gram-positive bacteria were constructed, and *Lactobacillus casei* was used as a host cell; however, it will be obvious to those skilled in that art that any Gram-positive bacteria other than *Lactobacillus casei* may be used as host cells, and that any Gram-negative bacteria other than Gram-positive bacteria, as well as other bacteria, may be expressed with the surface expression vectors.

Hereinafter, the present invention will be described in more detail with reference to examples. It will be obvious to those skilled in the art that these examples are merely to describe the present invention in more detail and the scope of the present invention according to the subject matter of the present invention is not limited by these examples.

Example 1: Construction of Surface Expression Vector pKV-Pald-pgsA-EGFP

To construct the EGFP expression vector, the gene encoding the EGFP protein was inserted into the C-terminus of PgsA using a surface expression vector prepared from pKV-Pald-PgsA-E7 (see Korean Patent No. 10-1471043), thereby obtaining the vector pKV-Pald-PgsA-EGFP that can be expressed on the surface of lactic acid bacteria.

First, the HPV16 E7 gene fused with pgsA was removed from the pKV-Pald-PgsA-E7 vector, and the EGFP-encoding gene was inserted into the vector. PCR was performed using the synthesized EGFP gene fragment as a template and primers of SEQ ID NO: 1 and SEQ ID NO: 2.

```
SEQ ID NO 1:
5' TGGTGGATCCGTGAGCAAGGGCGAGGAGCTG 3'

SEQ ID NO 2:
5' TGACTCTAGAACTAGTGTCGACGGTACCTTA
CTTGTACAGCTCGTCC 3'
```

As a result, a 755-bp fragment containing the EGFP gene was obtained. The fragment contained a BamHI restriction enzyme site at the 5' end and an XbaI restriction enzyme site at the 3' end. The obtained DNA fragment was treated with BamHI and XbaI restriction enzymes to obtain a 741-bp fragment.

pKV-Pald-PgsA-E7 was cleaved with BamHI and XbaI to remove the HPV16 E7 gene region, thus obtaining a vector fragment.

The E7 gene-containing DNA fragment cleaved with BamHI and XbaI was ligated with the vector cleaved with the same restriction enzymes, thereby obtaining pKV-Pald-PgsA-EGFP (FIG. 1).

Example 2: Improvement of Surface Expression Vector PgsA Motif

In this Example, improvement of the surface expression vector (pKV-Pald-PgsA-EGFP) constructed in Example 1 was performed to obtain PgsA gene fragments capable of more stably exhibiting a high expression rate in a lactic acid bacterium host.

First, to obtain PgsA fragments containing each of 1-60 a.a, 1-70 a.a, 1-80 a.a, 1-100 a.a and 1-188 a.a among PgsA fragments, PCR was performed using the surface expression vector (pKV-Pald-PgsA-EGFP) as a template and the following primers.

```
PgsA motif 1-60 a.a
SEQ ID NO 3:
5' TCGAGCATGCAATACCCACTTATTGCGATTTGCT 3'

SEQ ID NO 4:
5' TACGGGATCCACCAGAACCACCAGAACCACCAGAACCACCAGAACC
ACCTGAGAGTACGTCGTCAGAATACGTT 3'

PgsA motif 1-70 a.a
SEQ ID NO 5:
5' TCGAGCATGCAATACCCACTTATTGCGATTTGCT 3'

SEQ ID NO 6:
5' TACGGGATCCACCAGAACCACCAGAACCACCAGAACCACCAGAACC
ACCTCCCATCATAATATCGCCTACAAAT 3'

PgsA motif 1-80 a.a
SEQ ID NO 7:
5' TCGAGCATGCAATACCCACTTATTGCGATTTGCT 3'

SEQ ID NO 8:
5' TACGGGATCCACCAGAACCACCAGAACCACCAGAACCACCAGAACC
ACCTTTTTGCTCCGTTACTTTTTCAACA 3'

PgsA motif 1-100 a.a
SEQ ID NO 9:
5' TCGAGCATGCAATACCCACTTATTGCGATTTGCT 3'

SEQ ID NO 10:
5' TACGGGATCCACCAGAACCACCAGAACCACCAGAACCACCAGAACC
ACCTGCTACATAATCCGAGGCTCTAAAG 3'

PgsA motif 1-188 a.a
SEQ ID NO 11:
5' TCGAGCATGCAATACCCACTTATTGCGATTTGCT 3'

SEQ ID NO 12:
5' TACGGGATCCACCAGAACCACCAGAACCACCAGAACCACCAGAACC
ACCGACTTTCTGGTACGAAATTTTCTTT 3'
```

As a result, DNA fragments were obtained, which contained an aldolase promoter and contained the respective PgsA motif fragments. Each of the DNA fragments contained a SphI restriction enzyme site at the 5' end and a BamHI restriction enzyme site at the 3' end. The obtained DNA fragments were treated with SphI and BamHI. In addition, it was confirmed that the PgsA1 to PgsA5 motif fragments had the following nucleotide sequences, respectively.

```
PgsA 1-60 a.a fragment sequence (PgsA1)
SEQ ID NO 13:
5' ATGAAAAAAGAACTGAGCTTTCATGAAAAGCTGCTAAAGCTGACA
AAACAGCAAAAAAGAAAACCAATAAGCACGTATTTATTGCCATTCCG
ATCGTTTTTGTCCTTATGTTCGCTTTCATGTGGGCGGGAAAAGCGGAA
ACGCCGAAGGTCAAAACGTATTCTGACGACGTACTCTCA 3'

PgsA 1-70 a.a fragment sequence (PgsA2)
SEQ ID NO 14:
5' ATGAAAAAAGAACTGAGCTTTCATGAAAAGCTGCTAAAGCTGACA
AAACAGCAAAAAAGAAAACCAATAAGCACGTATTTATTGCCATTCCG
ATCGTTTTTGTCCTTATGTTCGCTTTCATGTGGGCGGGAAAAGCGGAA
ACGCCGAAGGTCAAAACGTATTCTGACGACGTACTCTCAGCCTCATTT
GTAGGCGATATTATGATGGGA 3'
```

-continued

PgsA 1-80 a.a fragment sequence (PgsA3)
SEQ ID NO 15:
5' ATGAAAAAAGAACTGAGCTTTCATGAAAAGCTGCTAAAGCTGACA

AAACAGCAAAAAAAGAAAACCAATAAGCACGTATTTATTGCCATTCCG

ATCGTTTTTGTCCTTATGTTCGCTTTCATGTGGGCGGGAAAAGCGGAA

ACGCCGAAGGTCAAAACGTATTCTGACGACGTACTCTCAGCCTCATTT

GTAGGCGATATTATGATGGGACGCTATGTTGAAAAAGTAACGGAGCAA

AAA 3'

PgsA 1-100 a.a fragment sequence (PgsA4)
SEQ ID NO 16:
5' ATGAAAAAAGAACTGAGCTTTCATGAAAAGCTGCTAAAGCTGACA

AAACAGCAAAAAAAGAAAACCAATAAGCACGTATTTATTGCCATTCCG

ATCGTTTTTGTCCTTATGTTCGCTTTCATGTGGGCGGGAAAAGCGGAA

ACGCCGAAGGTCAAAACGTATTCTGACGACGTACTCTCAGCCTCATTT

GTAGGCGATATTATGATGGGACGCTATGTTGAAAAAGTAACGGAGCAA

AAAGGGGCAGACAGTATTTTTCAATATGTTGAACCGATCTTTAGAGCC

TCGGATTATGTAGCA 3'

PgsA 1-188 a.a fragment sequence (PgsA5)
SEQ ID NO 17:
5' ATGAAAAAAGAACTGAGCTTTCATGAAAAGCTGCTAAAGCTGACA

AAACAGCAAAAAAAGAAAACCAATAAGCACGTATTTATTGCCATTCCG

ATCGTTTTTGTCCTTATGTTCGCTTTCATGTGGGCGGGAAAAGCGGAA

ACGCCGAAGGTCAAAACGTATTCTGACGACGTACTCTCAGCCTCATTT

GTAGGCGATATTATGATGGGACGCTATGTTGAAAAAGTAACGGAGCAA

AAAGGGGCAGACAGTATTTTTCAATATGTTGAACCGATCTTTAGAGCC

TCGGATTATGTAGCAGGAAACTTTGAAAACCCGGTAACCTATCAAAAG

AATTATAAACAAGCAGATAAAGAGATTCATCTGCAGACGAATAAGGAA

TCAGTGAAAGTCTTGAAGGATATGAATTTCACGGTTCTCAACAGCGCC

AACAACCACGCAATGGATTACGGCGTTCAGGGCATGAAAGATACGCTT

GGAGAATTTGCGAAGCAAAACCTTGATATCGTTGGAGCGGGATACAGC

TTAAGTGATGCGAAAAAGAAAATTTCGTACCAGAAAGTC 3'

The pKV-Pald-PgsA-EGFP was cleaved with SphI and BamHI, thus obtaining vector fragments from which the aldolase promoter and the PgsA gene region were removed.

The DNA fragments cleaved with SphI and BamHI, which contained the aldolase promoter and the respective PgsA motif fragment genes, were each ligated with the vector cleaved with the same restriction enzymes, thus obtaining improved vectors (FIGS. 2 to 6).

Meanwhile, to obtain PgsA fragments containing each of 25-60 a.a, 25-70 a.a and 25-100 a.a among PgsA fragments, PCR was performed using the surface expression vector (pKV-Pald-PgsA-EGFP) as a template and the following primers.

PgsA motif 25-60 a.a
SEQ ID NO 18:
5' CGCTGGATATCTACATGCACGTATTTATTGCCATTCCG 3'

SEQ ID NO 19:
5' TACGGGATCCACCAGAACCACCAGAACCACCAGAACCACCAGAAC

CACCTGAGAGTACGTCGTCAGAATACGTT 3'

PgsA motif 25-70 a.a
SEQ ID NO 20:
5' CGCTGGATATCTACATGCACGTATTTATTGCCATTCCG 3'

SEQ ID NO 21:
5' TACGGGATCCACCAGAACCACCAGAACCACCAGAACCACCAGAAC

CACCTCCCATCATAATATCGCCTACAAAT 3'

PgsA motif 25-100 a.a
SEQ ID NO 22:
5' CGCTGGATATCTACATGCACGTATTTATTGCCATTCCG 3'

SEQ ID NO 23:
5' TACGGGATCCACCAGAACCACCAGAACCACCAGAACCACCAGAAC

CACCTGCTACATAATCCGAGGCTCTAAAG 3'

As a result, DNA fragments containing the respective PgsA motif fragments were obtained. Each of the DNA fragments contained an EcoRV restriction enzyme site at the 5' end and a BamHI restriction enzyme site at the 3' end. The obtained DNA fragments were treated with EcoRV and BamHI to obtain fragments. In addition, it was confirmed that the PgsA motif fragments had the following nucleotide sequences.

PgsA 25-60 a.a fragment sequence (PgsA6)
SEQ ID NO 24:
5' CACGTATTTATTGCCATTCCGATCGTTTTTGTCCTTATGTTCGCT

TTCATGTGGGCGGGAAAAGCGGAAACGCCGAAGGTCAAAACGTATTCT

GACGACGTACTCTCA 3'

PgsA 25-70 a.a fragment sequence (PgsA7)
SEQ ID NO 25:
5' CACGTATTTATTGCCATTCCGATCGTTTTTGTCCTTATGTTCGCT

TTCATGTGGGCGGGAAAAGCGGAAACGCCGAAGGTCAAAACGTATTCT

GACGACGTACTCTCAGCCTCATTTGTAGGCGATATTATGATGGGA 3'

PgsA 25-100 a.a fragment sequence (PgsA8)
SEQ ID NO 26:
5' CACGTATTTATTGCCATTCCGATCGTTTTTGTCCTTATGTTCGCT

TTCATGTGGGCGGGAAAAGCGGAAACGCCGAAGGTCAAAACGTATTCT

GACGACGTACTCTCAGCCTCATTTGTAGGCGATATTATGATGGGACGC

TATGTTGAAAAAGTAACGGAGCAAAAAGGGGCAGACAGTATTTTTCAA

TATGTTGAACCGATCTTTAGAGCCTCGGATTATGTAGCA 3'

The pKV-Pald-PgsA-EGFP was cleaved with EcoRV and BamHI, thus obtaining vector fragments from which the PgsA gene region was removed.

Figure 7:
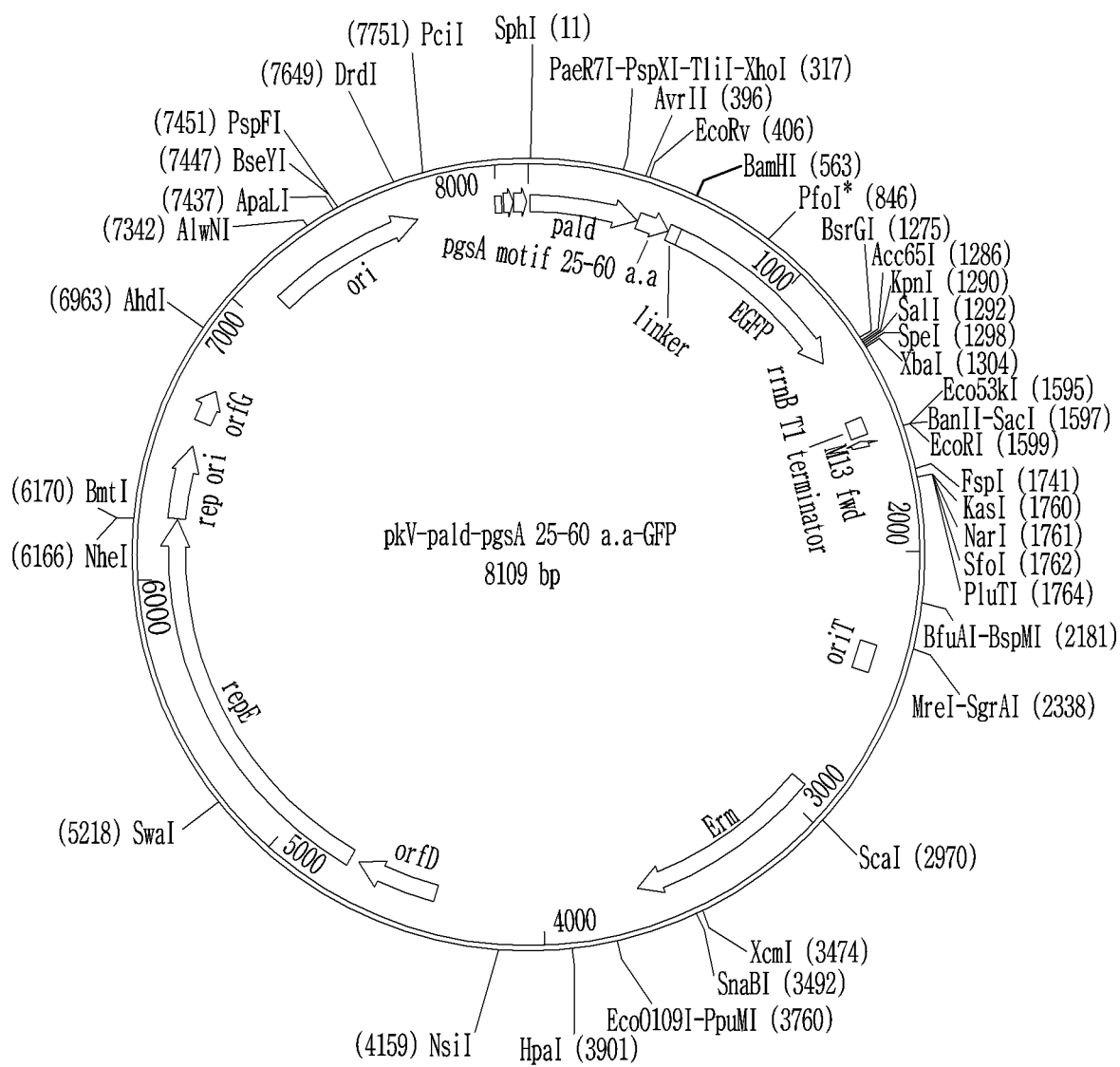
FIG. 7 shows a genetic map of the surface expression vector pKV-Pald-pgsA6 (PgsA motif 25-60 a.a-EGFP) according to the present invention, which uses *Lactobacillus casei* as a host.
Figure 8:
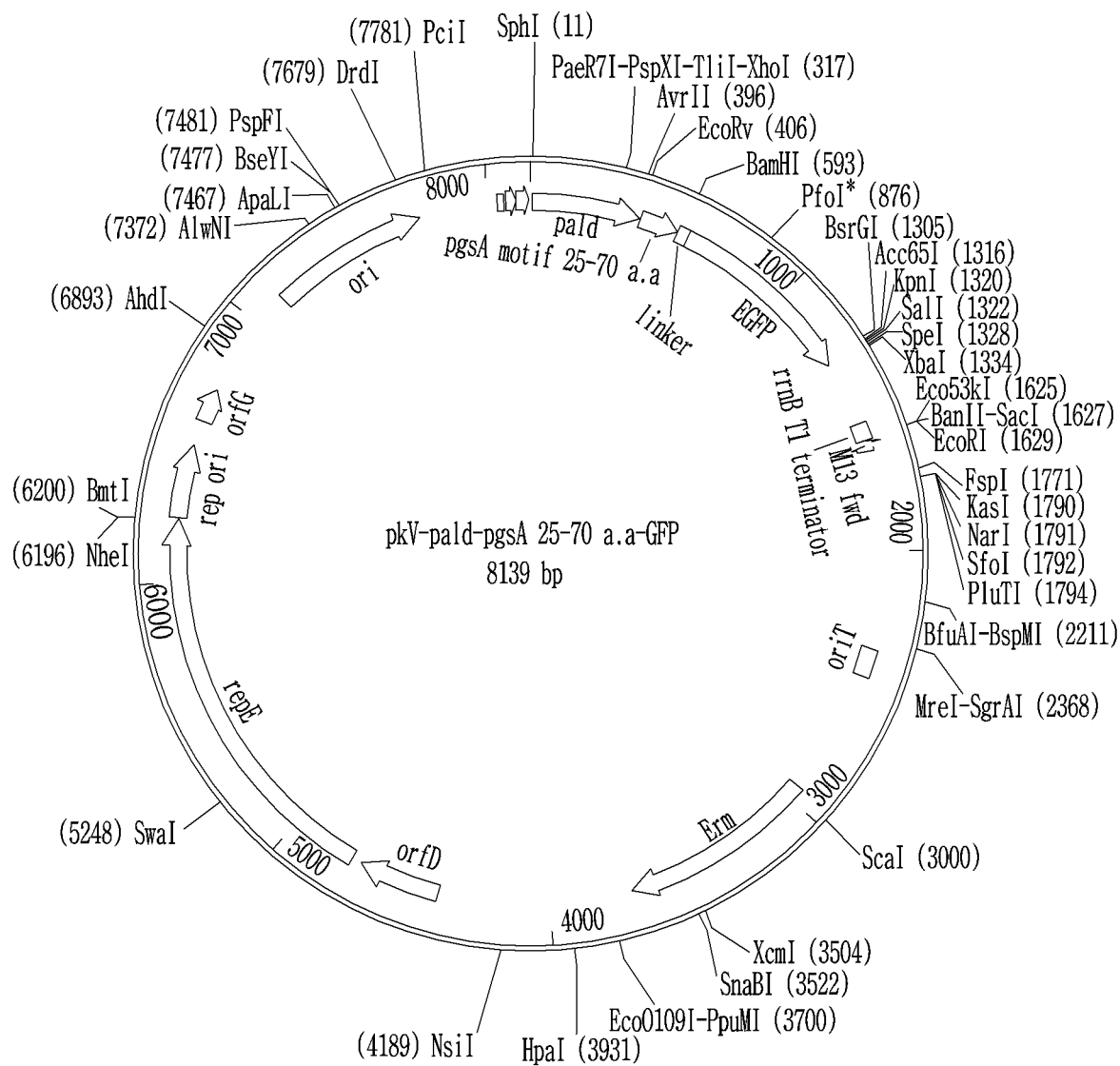
FIG. 8 shows a genetic map of the surface expression vector pKV-Pald-pgsA7 (PgsA motif 25-70 a.a-EGFP) according to the present invention, which uses *Lactobacillus casei* as a host.
Figure 9:
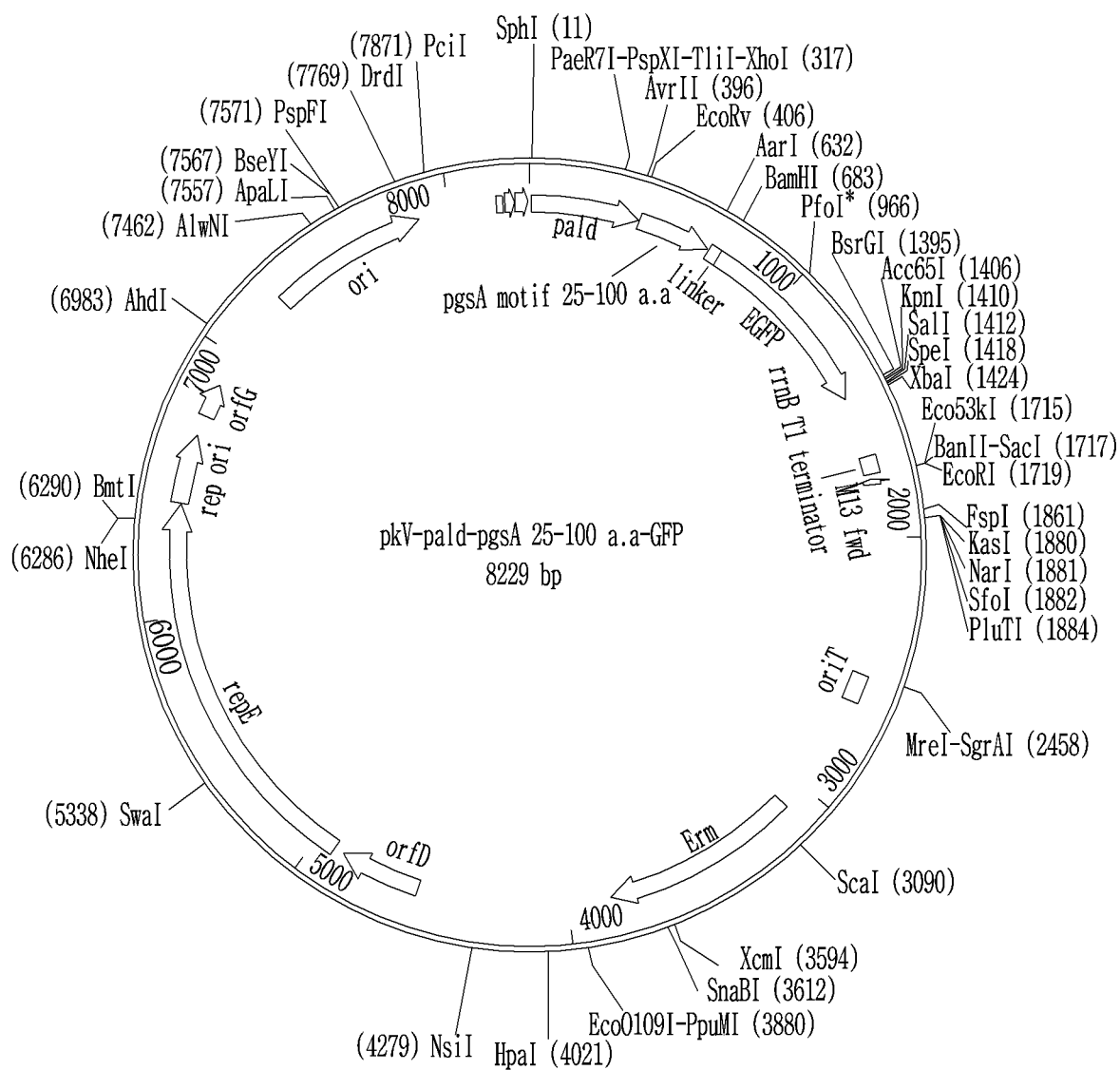
FIG. 9 shows a genetic map of the surface expression vector pKV-Pald-pgsA8 (PgsA motif 25-100 a.a-EGFP) according to the present invention, which uses *Lactobacillus casei* as a host.

The DNA fragments containing the respective PgsA motif gene fragments, which were cleaved with EcoRV and BamHI, were ligated with the vector cleaved with the same restriction enzymes, thus obtaining improved vectors (FIGS. 7 to 9).

Example 3: Analysis of Expression in Transformants Containing Improved PgsA Motif Surface Expression Vector In this Example, *Lactobacillus casei* was transformed with each of the improved PgsA motif surface expression vectors constructed in Example 2, the transformed recombinant *Lactobacillus casei* was cultured, and expression of the EGFP protein therein was analyzed. Examination was made as to whether the EGFP protein fused with any one of the improved pgsA1 to pgsA8 was expressed in the transformed recombinant *Lactobacillus casei*.

The recombinant *Lactobacillus casei* transformed with each of the PgsA motif fragment surface expression vectors was stationary-cultured in MRS medium (*Lactobacillus* MRS, Becton Dickinson and Company Sparks, USA) at 30° C. to induce surface expression of the EGFP protein fused with the C-terminus of any one of the poly-gamma-glutamate synthetase gene fragments pgsA1 to pgsA8.

The whole cell of the cultured *Lactobacillus casei* were subjected to SDS-polyacrylamide gel electrophoresis and Western blotting using a specific antibody against EGFP to confirm expression of the fusion protein.

Specifically, the transformed *Lactobacillus casei* in which gene expression was induced was denatured with a protein obtained at the same cell concentration, thus preparing a sample. The sample was analyzed by SDS-polyacrylamide gel electrophoresis, and then the protein fractions were transferred to polyvinylidene-difluoride (PVDF) membranes (Bio-Rad). The PVDF membranes to which the protein fractions had been transferred were blocked by shaking in a blocking buffer (50 mM Tris HCl, 5% skim milk, pH 8.0) for 1 hour, and then incubated for 1 hour with rabbit-derived polyclonal anti-EGFP primary antibodies which had been 1000-fold diluted in a blocking buffer. After completion of the incubation, the membranes were washed with buffer solution and incubated for 1 hour with HRP-conjugated anti-rabbit secondary antibodies which had been 10000-fold diluted in a blocking buffer. After completion of the incubation, the membranes were washed with buffer solution, and the washed membranes were color-developed for about 2 minutes by the addition of a substrate (lumigen PS-3 acridan, $H_2O_2$), and the specific binding between the EGFP-specific antibody and the fusion protein was observed with a CCD camera (FIG. 10).

Figure 10:
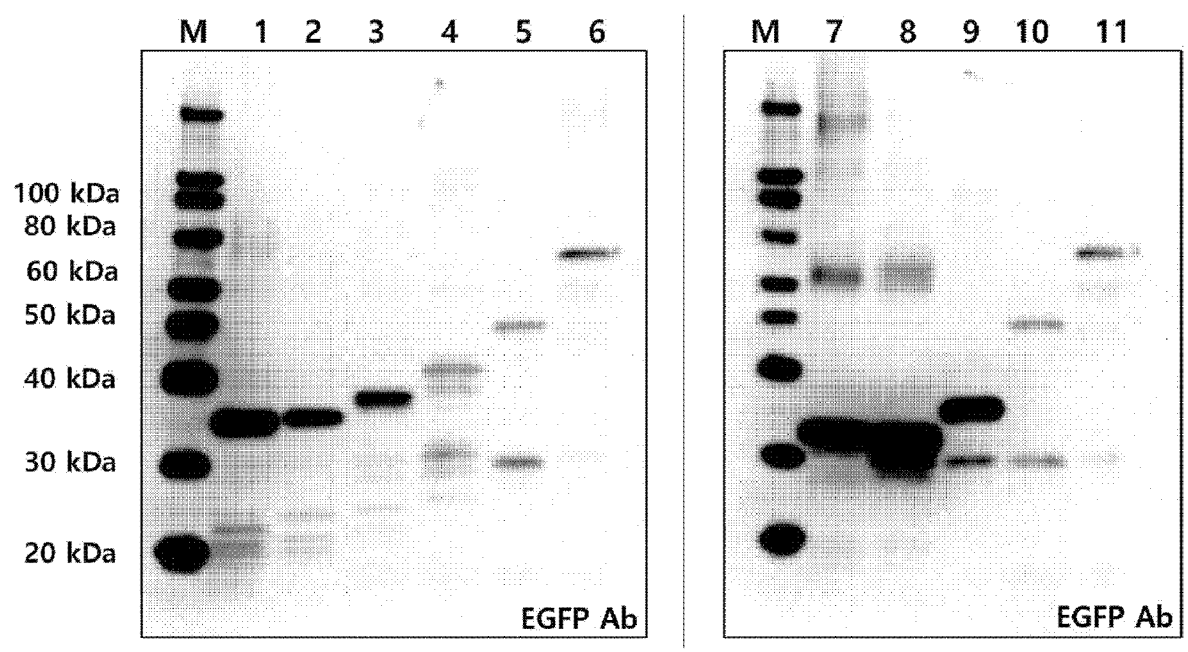
FIG. 10 depicts Western blot images showing surface expression of EGFP protein on *Lactobacillus casei* transformed with each of the surface expression vectors pKV-Pald-pgsA1 to pKV-Pald-pgsA8 of the present invention.

FIG. 10 shows expression patterns (lanes 6 and 11) in the *Lactobacillus casei* transformed with the pKV-Pald-pgsA recombinant expression vector into which non-improved pgsA as a control for comparison with the present invention was inserted, and expression patterns (lane 1 to 5 and lanes 7 to 10) in the *Lactobacillus casei* transformed with each of the recombinant expression vectors pKV-Pald-pgsA1 to pgsA8 into improved pgsA1 to pgsA8 according to the present invention were inserted, respectively.

Specifically, in FIG. 10, lane 1 represents the expression of EGFP in the recombinant *Lactobacillus casei* transformed with PgsA motif 1-60 a.a; lane 2 represents the expression of EGFP in the recombinant *Lactobacillus casei* transformed with PgsA motif 1-70 a.a; lane 3 represents the expression of EGFP in the recombinant *Lactobacillus casei* transformed with PgsA motif 1-80 a.a; and lane 4 represents the expression of EGFP in the recombinant *Lactobacillus casei* transformed with PgsA motif 1-100 a.a. In addition, lane 5 represents the expression of EGFP in the recombinant *Lactobacillus casei* transformed with PgsA motif 1-188 a.a, and lane 6 represents protein expression in the recombinant *Lactobacillus casei* transformed with pKV-Pald-PgsA-EGFP.

In addition, in FIG. 10, lane 7 represents the expression of EGFP in the recombinant *Lactobacillus casei* transformed with PgsA motif 25-60 a.a; lane 8 represents the expression of EGFP in the recombinant *Lactobacillus casei* transformed with PgsA motif 25-70 a.a; and lane 9 represents the expression of EGFP in the recombinant *Lactobacillus casei* transformed with PgsA motif 25-100 a.a. Furthermore, lane 10 represents the expression of EGFP in the recombinant *Lactobacillus casei* transformed with PgsA motif 1-188 a.a. Lane 11 represents protein expression in the recombinant *Lactobacillus casei* transformed with pKV-Pald-PgsA-EGFP.

It was confirmed that expression of the EGFP fusion protein by each of the surface expression vector containing each of the improved PgsA motif fragments was stronger than expression of the EGFP fusion protein by the non-improved pKV-Pald-pgsA-EGFP surface expression vector.

INDUSTRIAL APPLICABILITY

The present invention is directed to a novel vector that effectively expresses a foreign protein on the microbial surface using an outer-membrane protein (pgsA), which is derived from a *Bacillus* sp. strain and involved in the synthesis of poly-gamma-glutamate. The surface expression vector for expression of a target protein according to the present invention may stably express the target protein. In addition, the surface expression vector according to the present invention may constitutively express the target protein and, at the same time, may be effectively used to produce a necessary antigen for vaccine production by expression on the surface of a recombinant microorganism. Thus, the surface expression vector is industrially applicable.

SEQUENCE LIST FREE TEXT

SEQ ID NO 1:
5' TGGTGGATCCGTGAGCAAGGGCGAGGAGCTG 3'

SEQ ID NO 2:
5' TGACTCTAGAACTAGTGTCGACGGTACCTTACTTGTACAGCTCGT

CC 3'

SEQ ID NO 3:
5' TCGAGCATGCAATACCCACTTATTGCGATTTGCT 3'

SEQ ID NO 4:
5' TACGGGATCCACCAGAACCACCAGAACCACCAGAACCACCAGAAC

CACCTGAGAGTACGTCGTCAGAATACGTT 3'

SEQ ID NO 5:
5' TCGAGCATGCAATACCCACTTATTGCGATTTGCT 3'

SEQ ID NO 6:
5' TACGGGATCCACCAGAACCACCAGAACCACCAGAACCACCAGAAC

CACCTCCCATCATAATATCGCCTACAAAT 3'

SEQ ID NO 7:
5' TCGAGCATGCAATACCCACTTATTGCGATTTGCT 3'

SEQ ID NO 8:
5' TACGGGATCCACCAGAACCACCAGAACCACCAGAACCACCAGAAC
CACCTTTTTGCTCCGTTACTTTTTCAACA 3'

SEQ ID NO 9:
5' TCGAGCATGCAATACCCACTTATTGCGATTTGCT 3'

SEQ ID NO 10:
5' TACGGGATCCACCAGAACCACCAGAACCACCAGAACCACCAGAAC
CACCTGCTACATAATCCGAGGCTCTAAAG 3'

SEQ ID NO 11:
5' TCGAGCATGCAATACCCACTTATTGCGATTTGCT 3'

SEQ ID NO 12:
5' TACGGGATCCACCAGAACCACCAGAACCACCAGAACCACCAGAAC
CACCGACTTTCTGGTACGAAATTTTCTTT 3'

SEQ ID NO 13:
5' ATGAAAAAAGAACTGAGCTTTCATGAAAAGCTGCTAAAGCTGACA
AAACAGCAAAAAAGAAAACCAATAAGCACGTATTTATTGCCATTCCG
ATCGTTTTTGTCCTTATGTTCGCTTTCATGTGGGCGGGAAAAGCGGAA
ACGCCGAAGGTCAAAACGTATTCTGACGACGTACTCTCA 3'

SEQ ID NO 14:
5' ATGAAAAAAGAACTGAGCTTTCATGAAAAGCTGCTAAAGCTGACA
AAACAGCAAAAAAGAAAACCAATAAGCACGTATTTATTGCCATTCCG
ATCGTTTTTGTCCTTATGTTCGCTTTCATGTGGGCGGGAAAAGCGGAA
ACGCCGAAGGTCAAAACGTATTCTGACGACGTACTCTCAGCCTCATTT
GTAGGCGATATTATGATGGGA 3'

SEQ ID NO 15:
5' ATGAAAAAAGAACTGAGCTTTCATGAAAAGCTGCTAAAGCTGACA
AAACAGCAAAAAAGAAAACCAATAAGCACGTATTTATTGCCATTCCG
ATCGTTTTTGTCCTTATGTTCGCTTTCATGTGGGCGGGAAAAGCGGAA
ACGCCGAAGGTCAAAACGTATTCTGACGACGTACTCTCAGCCTCATTT
GTAGGCGATATTATGATGGGACGCTATGTTGAAAAAGTAACGGAGCAA
AAA 3'

SEQ ID NO 16:
5' ATGAAAAAAGAACTGAGCTTTCATGAAAAGCTGCTAAAGCTGACA
AAACAGCAAAAAAGAAAACCAATAAGCACGTATTTATTGCCATTCCG
ATCGTTTTTGTCCTTATGTTCGCTTTCATGTGGGCGGGAAAAGCGGAA
ACGCCGAAGGTCAAAACGTATTCTGACGACGTACTCTCAGCCTCATTT
GTAGGCGATATTATGATGGGACGCTATGTTGAAAAAGTAACGGAGCAA
AAAGGGGCAGACAGTATTTTTCAATATGTTGAACCGATCTTTAGAGCC
TCGGATTATGTAGCA 3'

SEQ ID NO 17:
5' ATGAAAAAAGAACTGAGCTTTCATGAAAAGCTGCTAAAGCTGACA
AAACAGCAAAAAAGAAAACCAATAAGCACGTATTTATTGCCATTCCG
ATCGTTTTTGTCCTTATGTTCGCTTTCATGTGGGCGGGAAAAGCGGAA
ACGCCGAAGGTCAAAACGTATTCTGACGACGTACTCTCAGCCTCATTT
GTAGGCGATATTATGATGGGACGCTATGTTGAAAAAGTAACGGAGCAA
AAAGGGGCAGACAGTATTTTTCAATATGTTGAACCGATCTTTAGAGCC
TCGGATTATGTAGCAGGAAACTTTGAAAACCCGGTAACCTATCAAAAG
AATTATAAACAAGCAGATAAAGAGATTCATCTGCAGACGAATAAGGAA
TCAGTGAAAGTCTTGAAGGATATGAATTTCACGGTTCTCAACAGCGCC
AACAACCACGCAATGGATTACGGCGTTCAGGGCATGAAAGATACGCTT
GGAGAATTTGCGAAGCAAAACCTTGATATCGTTGGAGCGGGATACAGC
TTAAGTGATGCGAAAAAGAAAATTTCGTACCAGAAAGTC 3'

SEQ ID NO 18:
5' CGCTGGATATCTACATGCACGTATTTATTGCCATTCCG 3'

SEQ ID NO 19:
5' TACGGGATCCACCAGAACCACCAGAACCACCAGAACCACCAGAAC
CACCTGAGAGTACGTCGTCAGAATACGTT 3'

SEQ ID NO 20:
5' CGCTGGATATCTACATGCACGTATTTATTGCCATTCCG 3'

SEQ ID NO 21:
5' TACGGGATCCACCAGAACCACCAGAACCACCAGAACCACCAGAAC
CACCTCCCATCATAATATCGCCTACAAAT 3'

SEQ ID NO 22:
5' CGCTGGATATCTACATGCACGTATTTATTGCCATTCCG 3'

SEQ ID NO 23:
5' TACGGGATCCACCAGAACCACCAGAACCACCAGAACCACCAGAAC
CACCTGCTACATAATCCGAGGCTCTAAAG 3'

SEQ ID NO 24:
5' CACGTATTTATTGCCATTCCGATCGTTTTTGTCCTTATGTTCGCT
TTCATGTGGGCGGGAAAAGCGGAAACGCCGAAGGTCAAAACGTATTCT
GACGACGTACTCTCA 3'

SEQ ID NO 25:
5' CACGTATTTATTGCCATTCCGATCGTTTTTGTCCTTATGTTCGCT
TTCATGTGGGCGGGAAAAGCGGAAACGCCGAAGGTCAAAACGTATTCT
GACGACGTACTCTCAGCCTCATTTGTAGGCGATATTATGATGGGA 3'

SEQ ID NO 26:
5' CACGTATTTATTGCCATTCCGATCGTTTTTGTCCTTATGTTCGCT
TTCATGTGGGCGGGAAAAGCGGAAACGCCGAAGGTCAAAACGTATTCT
GACGACGTACTCTCAGCCTCATTTGTAGGCGATATTATGATGGGACGC
TATGTTGAAAAAGTAACGGAGCAAAAAGGGGCAGACAGTATTTTTCAA
TATGTTGAACCGATCTTTAGAGCCTCGGATTATGTAGCA 3'

The invention claimed is:

1. A surface expression vector for expression of a target protein, the surface expression vector comprising:
   a gene encoding pgsA; and
   a gene encoding a target protein,
   wherein the gene encoding the pgsA consists of the nucleotide sequence of any one of SEQ ID NOs: 13 to 15 and 24 to 26.

2. The surface expression vector of claim 1, wherein the gene pgsA is derived from a *Bacillus* sp. strain that produces poly-gamma-glutamate.

3. The surface expression vector of claim 1, wherein a linker is inserted at a terminal end of the gene pgsA, and the gene encoding the target protein is inserted into the inserted linker.

4. The surface expression vector of claim 1, wherein a portion of the amino acid sequence of the target protein is removed or site-specifically mutated to favor surface expression of the target protein.

5. The surface expression vector of claim 1, wherein the vector comprises an aldolase promoter derived from lactic acid bacteria.

6. The surface expression vector of claim 1, wherein the vector is used to transform Gram-negative bacteria or Gram-positive bacteria.

7. A microorganism transformed with the surface expression vector of claim 1.

8. The microorganism of claim 7, wherein a microorganism which is used to obtain the transformed microorganism is a microorganism modified to favor cell-surface expression of the target protein so that it does not produce intracellular or extracellular proteases that are involved in degradation of the expressed target protein.

9. The microorganism of claim 7, wherein the microorganism is lactic acid bacteria.

10. A method for cell surface expression of a target protein, the method comprising steps of:
    expressing the target protein on a cell surface by culturing the transformed microorganism of claim 7; and
    recovering cells having the target protein expressed on the surface thereof.

11. The method of claim 10, wherein the target protein is any one selected from the group consisting of a hormone, a hormone analogue, an enzyme, an enzyme inhibitor, a signaling protein or a portion thereof, an antibody or a portion thereof, a single-chain antibody, a binding protein, a binding domain, a peptide, an antigen, an adhesion protein, a structural protein, a regulatory protein, a toxin protein, a cytokine, a transcription regulatory factor, a blood coagulation factor, and a plant defense-inducing protein.

12. A method of inducing humoral immunity or cell-mediated immunity, comprising administering cells produced by the method of claim 11 and having an antigen expressed on the surface thereof to a vertebrate animal except for a human.

13. A method of expressing a target protein on a surface of a Gram-negative or Gram-positive host cell, the method comprising steps of:
    (a) constructing a recombinant vector by inserting a gene encoding a target protein into the surface expression vector of claim 6;
    (b) transforming the Gram-negative or Gram-positive host cell with the recombinant vector; and
    (c) expressing the target protein on the surface of the host cell by culturing the transformed host cell.

14. An expression vector, comprising:
    an aldolase promoter;
    a pgsA gene from a *Bacillus* sp. encoding a poly-gamma-glutamate synthetase complex surface-anchoring motif consisting of the nucleotide sequence of any one of SEQ ID Nos: 13-15 and 24-26;
    a linker at a terminal end of the pgsA gene sequence; and
    a gene encoding a target protein.

* * * * *